US010888117B2

(12) United States Patent
Danek

(10) Patent No.: US 10,888,117 B2
(45) Date of Patent: Jan. 12, 2021

(54) APPARATUS FOR PRODUCING AN AEROSOL FOR INHALATION BY A PERSON

(71) Applicant: RESPIRA TECHNOLOGIES, INC., Los Angeles, CA (US)

(72) Inventor: Mario Danek, Los Angeles, CA (US)

(73) Assignee: RESPIRA TECHNOLOGIES, INC., West Hollywood, CA (US)

(*) Notice: Subject to any disclaimer, the term of this patent is extended or adjusted under 35 U.S.C. 154(b) by 0 days.

(21) Appl. No.: 16/657,732

(22) Filed: Oct. 18, 2019

(65) Prior Publication Data

US 2020/0120989 A1 Apr. 23, 2020

Related U.S. Application Data

(60) Provisional application No. 62/747,260, filed on Oct. 18, 2018, provisional application No. 62/794,274, filed on Jan. 18, 2019.

(51) Int. Cl.
*A24F 47/00* (2020.01)
*A24B 15/167* (2020.01)
(Continued)

(52) U.S. Cl.
CPC .......... *A24F 47/002* (2013.01); *A24B 15/167* (2016.11); *A24F 40/05* (2020.01);
(Continued)

(58) Field of Classification Search
None
See application file for complete search history.

(56) References Cited

U.S. PATENT DOCUMENTS 5,435,282 A * 7/1995 Haber ............... A61M 15/0065
128/200.14
5,518,179 A 5/1996 Humberstone
(Continued)

FOREIGN PATENT DOCUMENTS

EP 0718046 A2 6/1996
EP 2886185 A1 6/2015
(Continued)

OTHER PUBLICATIONS

Borders, Brett, "What is Nanoemulsified CBD?", Aug. 8, 2018, <http://brettborders.net/what-is-nanoemulsified-cbd-oil/> (Year: 2018).*
(Continued)

*Primary Examiner* — Michael H. Wilson
*Assistant Examiner* — Katherine A Will
(74) *Attorney, Agent, or Firm* — Chad D. Tillman; Tillman Wright, PLLC

(57) ABSTRACT

A disposable cartridge is disclosed for use with an electronic device for producing an aerosol for inhalation by a person. The cartridge comprises a liquid container containing a liquid which when aerosolized is intended for inhalation by a person; and a transducer that, when actuated, causes the liquid from the container to be aerosolized such that the aerosol may be inhaled by a person. In various embodiments, the liquid comprises: a liposomal carrier; a liquid mixture having an active agent entrapped by liposomes; and a liquid mixture comprising a nanodispersion. The liquid may include nicotine, tetrahydrocannabinol, cannabidiol, or nanoparticles formed by an oil droplet covered by a monolayer of phosphatidylcholine. The transducer preferably comprises a mesh material with the transducer and the mesh material forming a piezo mesh disk for aerosolizing the liquid.

20 Claims, 19 Drawing Sheets

(51) Int. Cl.
    *B65D 83/00* (2006.01)
    *A61K 9/127* (2006.01)
    *A61K 31/465* (2006.01)
    *A61K 31/352* (2006.01)
    *A61M 15/00* (2006.01)
    *A24F 40/05* (2020.01)

(52) U.S. Cl.
    CPC .......... *A61K 9/127* (2013.01); *A61K 31/352* (2013.01); *A61K 31/465* (2013.01); *A61M 15/009* (2013.01); *B65D 83/0011* (2013.01); *A61M 2205/0294* (2013.01)

(56) References Cited

U.S. PATENT DOCUMENTS

| | | |
|---|---|---|
| 5,586,550 A | 12/1996 | Ivri et al. |
| 5,938,117 A | 8/1999 | Ivri |
| 5,970,974 A | 10/1999 | Van Der Linden et al. |
| 6,196,218 B1 | 3/2001 | Voges |
| 6,427,682 B1 | 8/2002 | Klimowicz et al. |
| 6,748,944 B1 | 6/2004 | DellaVecchia et al. |
| 9,352,108 B1 | 5/2016 | Reed et al. |
| 10,137,261 B2 | 11/2018 | Knudsen |
| 10,334,888 B2 | 7/2019 | Cameron et al. |
| 10,349,676 B2 | 7/2019 | King et al. |
| 2004/0204354 A1* | 10/2004 | Nelson .................. A61K 9/127 424/450 |
| 2004/0206351 A1 | 10/2004 | McFarland |
| 2005/0011514 A1 | 1/2005 | Power et al. |
| 2007/0267010 A1 | 11/2007 | Fink et al. |
| 2009/0050142 A1 | 2/2009 | Hamano |
| 2009/0095821 A1 | 4/2009 | Feriani |
| 2010/0044460 A1 | 2/2010 | Sauzade |
| 2011/0108025 A1 | 5/2011 | Fink et al. |
| 2011/0168194 A1 | 7/2011 | Hon |
| 2011/0265806 A1 | 11/2011 | Alarcon et al. |
| 2012/0236680 A1 | 9/2012 | Panagiotou et al. |
| 2012/0266870 A1 | 10/2012 | Denyer et al. |
| 2013/0079732 A1 | 3/2013 | Burt et al. |
| 2013/0267864 A1 | 10/2013 | Addington |
| 2013/0269684 A1 | 10/2013 | Patton |
| 2015/0165137 A1 | 6/2015 | Mullinger |
| 2015/0257447 A1 | 9/2015 | Sullivan |
| 2016/0001019 A1 | 1/2016 | Fink et al. |
| 2016/0192708 A1 | 7/2016 | Demeritt et al. |
| 2016/0213866 A1 | 7/2016 | Tan |
| 2017/0119059 A1 | 5/2017 | Zuber et al. |
| 2017/0172977 A1* | 6/2017 | Kleidon .............. A61K 31/352 |
| 2017/0281701 A1 | 10/2017 | Kan |
| 2017/0368273 A1* | 12/2017 | Rubin .................. A61M 11/042 |
| 2018/0146710 A1 | 5/2018 | Bessant et al. |
| 2018/0289907 A1 | 10/2018 | Marmur et al. |
| 2019/0045834 A1 | 2/2019 | Fuisz et al. |
| 2019/0299171 A1 | 10/2019 | Xiong et al. |
| 2020/0060338 A1 | 2/2020 | Danek |
| 2020/0060349 A1 | 2/2020 | Danek |

FOREIGN PATENT DOCUMENTS

| | | |
|---|---|---|
| EP | 2523710 B1 | 10/2015 |
| EP | 3228345 A1 | 11/2017 |
| EP | 3469929 A1 | 12/2019 |
| FR | 3064490 A1 | 10/2018 |
| GB | 2524856 A | 10/2015 |
| KR | 20047018035 A | 1/2009 |
| KR | 2010-0097807 A | 9/2010 |
| KR | 1020120104964 | 9/2012 |
| WO | 199301091 A1 | 6/1993 |
| WO | 2000050111 A1 | 8/2000 |
| WO | 2014167515 A1 | 10/2014 |
| WO | 2016019353 A1 | 2/2016 |
| WO | 2016076178 A1 | 5/2016 |
| WO | 2017076590 A1 | 5/2017 |
| WO | 2017149165 A1 | 9/2017 |
| WO | 2017175218 A2 | 10/2017 |
| WO | 2018002926 A1 | 1/2018 |
| WO | 2019239217 A1 | 12/2019 |
| WO | 2020041641 A1 | 2/2020 |
| WO | 2020081874 A1 | 4/2020 |

OTHER PUBLICATIONS

Uchiyama et al. "Determination of Chemical Compounds Generated from Second-generation E-cigarettes Using a Sorbent Cartridge Followed by a Two-step Elution Method", Analytical Sciences, vol. 32, pp. 549-556, May 2016. (8 pages).

Vecellio. "The mesh nebuliser: a recent technical innovation for aerosol delivery", Breathe, vol. 2, pp. 252-260, Mar. 2006, (9 pages).

Microfluidics "Microfluidizer Processor User Guide. Innovation Through Microfluidizer Processor Technology" Dec. 2014. (10 pages).

Sahiti et al. "Nebulizers: A Review Paper", International Journal of Advanced Research in Computer Science, vol. 8, No. 5, May-Jun. 2017 ISSN No. 0976-5697, pp. 1697-1699. (3 pages).

El-Hellani et al. "Nicotine and Carbonyl Emissions From Popular Electronic Cigarette Products: Correlation to Liquid Composition and Design Characteicstics", Nicotine & Tobacco Research, 2018, 215-223 doi:10.1093/ntr/ntw280/, pp. 216-223. (9 pages).

Gillman et al. "Effect of variable power levels on the yield of total aerosol mass and formation of aldehydes in e-cigarette aerosols", Regulatory Toxicology and Pharmacology, vol. 75, 2016, pp. 58-65. (8 pages).

Swain et al. "Excipients and its Variation in Pharmaceutical Aerosol Formulation: A Review", Innovat Internation Journal of Medical & Pharmaceutical Sciences, vol. 1(1), 2016, pp. 4-8. (5 pages).

Green et al. "Pharmaceutical Aerosols—Enhancing the Metered Dose Inhaler", DuPont Central Research & Development. (10 pages).

Klager et al. "Flavoring Chemicals and Aldehydes in E-Cigarette Emissions", Environmental Science & Technology, vol. 51, pp. 10806-10813. (8 pages).

Wang et al. "A Device-Independent Evaluation of Carbonyl Emission from Heated Electronic Cigarette Solvents", PLOS ONE | DOI.10.1371/journal.pone.0169811, Jan. 11, 2017, pp. 1-14. (14 pages).

Philips InnoSpire Go—Portable Mesh Nebulizer, Highlights and Specifications, HH1342/00, version 5.0.1, Dec. 12, 2017 (2 pages).

Jensen et al. "Hidden Formaldehyde in E-Cigarette Aerosols", New England Journal of Medicine, Jan. 2015. (7 pages).

Jensen et al. "Hidden Formaldehyde in E-Cigarette Aerosols", Supplementary Appendix, New England Journal of Medicine, Jan. 2015. (3 pages).

Geiss et al. "Correlation of volatile carbonyl yields emitted by e-cigarettes with the temperature of the heating coil and the perceived sensorial quality of the generated vapours", International Journal of Hygiene and Environmental Health, vol. 219, pp. 268-277. (10 pages).

Farsalinos et al. "Carbonyl Emission in E-cigarette Aerosol: A Systematic Review and Methodological Considerations", Frontiers in Physiology, vol. 8, Article 1119, Jan. 11, 2018, pp. 1-14. (14 pages).

Olszewski et al. "A silicon-based MEMS vibrating mesh nebulizer for inhaled drug delivery", ScienceDirect, Procedia Engineering, vol. 168, pp. 1521-1524. (5 pages).

Herrington et al. "Electronic cigarette solutions and resultant aerosol profiles", Journal of Chromatography A, vol. 1418, pp. 192-199, 2015. (8 pages).

Hawkins et al. "Vibrating Mesh Nebulizer Reference Design", Microchip Technology Inc., AN2265. 2016-2017. (50 pages).

Rudokas et al. "Liposome Delivery Systems for Inhalation: A Critical Review Highlighting Formulation Issues and Anticancer Applications", Medical Principles and Practice, 2016;25(suppl 2), pp. 60-72, 2016. (13 pages).

(56) References Cited

OTHER PUBLICATIONS

Prichard et al. "Mesh nebulizers have become the first choice for new nebulized pharmaceutical drug developments", Therapeudic Delivery, vol. 9(2), Oct. 17, 2017, pp. 121-136. (16 pages).

Akbarzadeh et al. "Liposome: classification, preparation, and applications", Nanoscale Researh Letters, Nano Review, vol. 8:102. (9 pages).

Weir. "Juul users inhaling chemicals not listed". YaleNews, Jul. 30, 2019. (3 pages).

Ari. "Jet, Ultrasonic, and Mesh Nebulizers: An Evaluation of Nebulizers for Better Clinical Outcomes", Georgia State University, Respiratory Therapy Faculty Publications, Department of Respiratory Therapy, Eurasian J Pulmonol 2014; 16: 1-7, pp. 1-7. (8 pages).

Omron Mesh Nebulizer Micro AIR U100 (NE-U100-E) Instruction Manual, Nov. 2017. (32 pages).

"International Search Report" and "Written Opinion" of the International Search Authority (ISA/US) in Respira Technologies, Inc., International Patent Application Serial No. PCT/US2019/047790, dated Nov. 5, 2019 (12 pages).

"International Search Report" and "Written Opinion of the International Searching Authority" (ISA/US) in Respira Technologies, Inc., International Patent Application Serial No. PCT/US2019/056830, dated Mar. 10, 2020 (12 pages).

European patent application 16163666 submitted as priority document in PCT/IL2017/050402, made publicly available by WIPO through publication of the international application on Oct. 12, 2017, 22 pages.

European patent application 16176635 submitted as priority document in PCT/IL2017/050402, made publicly available by WIPO through publication of the international application on Oct. 12, 2017, 31 pages.

European patent application 16187618 submitted as priority document in PCT/IL2017/050402, made publicly available by WIPO through publication of the international application on Oct. 12, 2017, 51 pages.

European patent application 17155046 submitted as priority document in PCT/IL2017/050402, made publicly available by WIPO through publication of the international application on Oct. 12, 2017, 87 pages.

\* cited by examiner

148
144
148
146

Vibrating Piezo Mesh Disk

Liquid is drawn through the holes to produce droplets of consitent size

Cross section of a hole in the piezo mesh disk

400 aerosol for inhalation

142
144
146 aerosol

The result is fine particle, low velocity aerosol that is optimum for central and deep lung deposition

FIG. 15

APPARATUS FOR PRODUCING AN AEROSOL FOR INHALATION BY A PERSON

CROSS-REFERENCE TO RELATED APPLICATION

The present application is a nonprovisional patent application of, and claims priority under 35 U.S.C. § 119(e) to, each of: U.S. provisional patent application 62/747,260, filed Oct. 18, 2018, the disclosure of which is incorporated herein by reference; and U.S. provisional patent application 62/794,274, filed Jan. 18, 2019, the disclosure of which is incorporated herein by reference.

COPYRIGHT STATEMENT

Any new and original work of authorship in this document is subject to copyright protection under the copyright laws of the United States and other countries. Reproduction by anyone of this document as it appears in official governmental records is permitted, but otherwise all other copyright rights whatsoever are reserved.

BACKGROUND OF THE INVENTION

The invention generally relates to apparatus, systems, and methods for producing an aerosol for inhalation by a person, whether intended for personal or recreational use, or for the administration of medicines.

Vaping has been rapidly increasing in popularity, primarily because vaping provides a convenient, discreet, and presumably benign way to self-administer nicotine, cannabis, drugs or other micronutrients. Indeed, there is a common belief that vaping is healthier than smoking cigarettes; vaping purportedly lets smokers avoid dangerous chemicals inhaled from regular cigarettes while still getting nicotine. Vaping also can be used for cannabis.

Vaping is performed using a vaporizer. A vaporizer includes a vape pen or a cigarette style vape, referred to by many as an e-cigarette or "eCig". A vape pen generally is an elongate, thin, and stylized tube that resembles a fancy pen. In contrast, an e-cigarette resembles an actual cigarette. The e-cigarette is usually small in size (usually smaller and more discreet than vape pens), easily portable, and easy to use.

A common vaporizer comprises a container, which may be a tank—which is typically refillable, or a cartridge—which is typically single-use and not refillable. The tank or cartridge holds a liquid often referred to as an e-liquid or e-juice. Tanks are made out of polycarbonate plastic, glass, or stainless steel. The vaporizer also includes a mouthpiece for inhaling by a person through the mouth; an atomizer comprising a tiny heating element that converts the liquid into tiny, airborne droplets that are inhaled; and a controller for turning on the atomizer. Many vape pens are mouth-activated and turn on automatically when a person inhales. Others vape pins are button activated and require the person to push a button to activate the atomizer. Vaporizers are electrically powered using one or more batteries. The batteries typically are lithium ion batteries that are rechargeable and primarily are used to heat the heating element of the atomizer. A charger usually accompanies a vaporizer when purchased for charging the batteries. The charger may be a USB charger, car charger, or wall charger, and such chargers are generally very similar to phone chargers.

The battery-powered vaporizer produces vapor from any of a variety of liquids and liquid mixtures, especially those containing nicotine or cannabinoids. Many different types and flavors are available. Moreover, the liquids can be non-medicated (i.e., containing no nicotine or other substances—just pure vegetable glycerin and flavoring), or the liquids can contain nicotine or even in some instances if and where legal, the liquids can contain THC/CBD. The liquids also may contain one or more of a variety of flavors as well as micronutrients such as, for example, vitamin B12. A person can mix the liquids for use with a vape pen. E-cigarettes typically are purchased with prefilled cartridges. The heating element turns the contents of the liquids into an aerosol—the vapor—that is inhaled into the lungs and then exhaled by the person. Perhaps one of the most popular vaporizers today is known as the "JUUL", which is a small, sleek device that resembles a computer USB flash drive.

It is believed that while promoted as healthier than traditional cigarette use, vaping actually may be more dangerous. Propylene glycol, vegetable glycerin and combinations or methylations thereof, are chemicals that are often mixed with nicotine, cannabis, or hemp oil for use in vaporizers. Propylene glycol is the primary ingredient in a majority of nicotine-infused e-cigarette liquids. Unfortunately, at high temperatures propylene glycol converts into tiny polymers that can wreak havoc on lung tissue. In particular, scientists know a great deal about propylene glycol. It is found in a plethora of common household items—cosmetics, baby wipes, pharmaceuticals, pet food, antifreeze, etc. The U.S. Food and Drug Administration and Health Canada have deemed propylene glycol safe for human ingestion and topical application. But exposure by inhalation is another matter. Many things are safe to eat but dangerous to breathe. Because of low oral toxicity, propylene glycol is classified by the FDA as "generally recognized as safe" (GRAS) for use as a food additive, but this assessment was based on toxicity studies that did not involve heating and breathing propylene glycol. Indeed, a 2010 study published in the International Journal of Environmental Research and Public Health concluded that airborne propylene glycol circulating indoors can induce or exacerbate asthma, eczema, and many allergic symptoms. Children were said to be particularly sensitive to these airborne toxins. An earlier toxicology review warned that propylene glycol, ubiquitous in hairsprays, could be harmful because aerosol particles lodge deep in the lungs and are not respirable.

Moreover, when propylene glycol is heated, whether by a red-hot metal coil of a heating element of a vaporizer or otherwise, the potential harm from inhalation exposure increases. It is believed that high voltage heat transforms the propylene glycol and other vaping additives into carbonyls. Carbonyls are a group of cancer-causing chemicals that includes formaldehyde, which has been linked to spontaneous abortions and low birth weight. A known thermal breakdown product of propylene glycol, formaldehyde is an International Agency for Research on Cancer group 1 carcinogen!

Prevalent in nicotine e-cig products and present in some vape oil cartridges, FDA-approved flavoring agents pose additional risks when inhaled rather than eaten. The flavoring compounds smooth and creamy (diacetyl and acetyl propionyl) are associated with respiratory illness when inhaled in tobacco e-cigarette devices. Another hazardous-when-inhaled-but-safe-to-eat flavoring compound is Ceylon cinnamon, which becomes cytotoxic when aerosolized.

When a heating element gets red hot in a vaporizer, the liquid undergoes a process called "smoldering", which is a technical term for what is tantamount to "burning"; while much of the liquid is vaporized and atomized, a portion of the liquid undergoes pyrolysis or combustion. In that sense, most of the vaporizers that have flooded the commercial market may not be true vaporizers.

Additionally, clearance mechanisms of the lung, like all major points of contact with the external environment, have evolved to prevent the invasion of unwanted airborne particles from entering the body. Airway geometry, humidity and clearance mechanisms contribute to this filtration process.

In view of the foregoing, it is believed that a need exists for a vaporizer that provides an aerosol of the desired chemicals without the harmful byproducts that arise from smoldering. It is also believed that a need exists for a vaporizer that effectively and efficiently produces a vapor cloud that is not inhibited by the body's natural filtration process. This and other needs are believed to be met by embodiments in accordance with one or more aspects and features of the invention.

SUMMARY OF THE INVENTION

The invention includes many aspects and features. Moreover, while many aspects and features relate to, and are described in, the context of vaping, the invention is not limited to use only in such context. Indeed, depending on the context of use, the electronic device of the invention may be considered a vaporizer and may be in the form of a vape pen or e-cigarette. Indeed, those who vape may come to refer to embodiments of the invention as a vape pen even though heat is not utilized to create the aerosol that is inhaled. In the delivery of pharmaceuticals, patients may come to refer to embodiments of the invention as a nebulizer even though a gas transport (e.g., compressed gas) is not utilized and even though the aerosol that is produced in accordance with the invention may have a smaller particle size than the mist produced by common nebulizers. Other separate and distinct contexts of use of embodiments of the invention may similarly result in different nomenclature of the embodiments of the invention. Nonetheless, while the appearance and form factor of embodiments of the invention may vary depending on such contexts of use, the basic components and operation remain the same, except where otherwise described below.

In an aspect of the invention, an electronic device for producing an aerosol for inhalation by a person comprises: a mouthpiece; a liquid container for containing a liquid; a mesh assembly comprising a mesh material and a piezoelectric material. The mesh material is configured to vibrate when the piezoelectric material is actuated whereby the aerosol is produced when the mesh material is in contact with a liquid of the container such that the aerosol may be inhaled through the mouthpiece. The mouthpiece, the container, and the mesh assembly are located in-line along a longitudinal axis of the electronic device between opposite longitudinal ends of the electronic device, with the mesh assembly extending between and separating the mouthpiece and the container. The mesh material has a rigidity sufficient to prevent oscillations of varying amplitudes during actuation of the piezoelectric material of the mesh assembly whereby the aerosol is consistently produced.

In a feature, the electronic device has a size and shape configured to be gripped and held by hand during use of the electronic device.

In a feature, the mesh assembly comprises a piezo mesh disk. The mesh assembly preferably comprises an annular ring and the mesh material preferably is located within the area bounded by the annual ring.

In a feature, the mesh material is flat.

In a feature, the mesh material is dome-shaped.

In a feature, the mesh material is constructed from a metal alloy.

In a feature, the mesh material is produced by electroplating.

In a feature, the mesh material is produced by laser cutting.

In a feature, the mesh assembly comprises a plurality of vibrating meshes.

In a feature, the mesh assembly comprises two vibrating meshes.

In a feature, the mesh assembly comprises a double vibrating mesh.

In a feature, the mesh material is in the form of a mesh plate.

In a feature, the mesh material comprises between 500 holes and 6,000 holes, inclusive. Holes in the mesh material preferably are tapered and each preferably has a diameter of approximately three micrometers.

In a feature, the electronic device further comprises a sensor that detects when a person inhales, and wherein the mesh assembly is actuated in response to the detection of inhalation by a person.

In another aspect, an electronic device for producing an aerosol for inhalation by a person comprises: a mouthpiece located at one of opposite longitudinal ends of the electronic device; a liquid container; a transducer that when actuated causes a liquid from the container to be aerosolized such that the aerosol may be inhaled from the electronic device by a person through the mouthpiece; and circuitry and a power supply for actuating the transducer; wherein the mouthpiece, the liquid container, and the transducer are located in-line along a longitudinal axis of a housing of the electronic device extending between the opposite longitudinal ends of the electronic device; wherein the liquid container is located between and separates the transducer and the mouthpiece; and wherein the liquid container and the transducer are contained within a cartridge that is insertable into and removable from the housing of the electronic device, whereby the liquid container and the transducer are replaceable by the person when the liquid in the container is depleted.

In a feature, the electronic device further comprises a vibrating structure that is configured to be in contact with a liquid contained in the liquid container, and wherein actuation of the transducer causes vibrations of the transducer that result, in turn, in vibration of the vibrating structure.

In a feature, the vibrating structure does not comprise a vibrating mesh material.

In a feature, the transducer comprises a piezoelectric crystal.

In a feature, the piezoelectric crystal vibrates at a frequency of between 0.5 MHz to 5.0 MHz.

In a feature, the piezoelectric crystal vibrates at a frequency of between 1.2 MHz and 2.4 MHz.

In a feature, the electronic device further comprises an interface contained in the cartridge and located between the transducer and the liquid container, the interface comprising a coupling agent configured to transmit vibrations from the transducer to a liquid in the liquid container and configured to insulate the liquid in the liquid container from heat generated by the transducer.

In a feature, the coupling agent comprises a fluid.

In a feature, the coupling agent comprises a gel.

In a feature, the interface comprises a membrane.

In a feature, the membrane is hydrophobic.

In a feature, the membrane contains the coupling agent.

In a feature, the transducer comprises a piezoelectric crystal that vibrates at a high frequency when electrical current is applied, and a transducer horn that is in contact with the liquid to be aerosolized, wherein vibrations of the crystal are transmitted by the transducer horn to the liquid. The transducer preferably comprises a piezoelectric crystal that vibrates at a high frequency when electrical current is applied, and a transducer horn that is in contact with the interface, wherein vibrations of the crystal are transmitted by the transducer horn to the interface which then transmits the vibrations to the liquid. The vibrations transmitted by the transducer horn preferably cause a mesh to vibrate such that liquid passes through apertures in the mesh to form an aerosol, the mesh preferably comprises a mesh plate that is in contact with the liquid, and the mesh plate preferably comprises between 500 holes and 6,000 holes, inclusive. The holes in the mesh plate preferably are tapered, and holes in the mesh plate each preferably has a diameter of approximately three micrometers.

In an aspect of the invention, a disposable cartridge for use with an electronic device for producing an aerosol for inhalation by a person comprises: a liquid container containing a liquid which when aerosolized is intended for inhalation by a person; and a transducer that, when actuated, causes the liquid from the container to be aerosolized such that the aerosol may be inhaled by a person; wherein the liquid to be aerosolized comprises a liposomal carrier. In this respect, the liquid is considered to be a liquid mixture.

In a feature, the liposomal carrier comprises a liposomal nanoemulsion.

In a feature, the liquid comprises nanoparticles.

In a feature, the liquid comprises nicotine.

In a feature, the liquid comprises encapsulated tetrahydrocannabinol.

In a feature, the liquid comprises encapsulated cannabidiol.

In a feature, the liquid comprises an aqueous liquid.

In a feature, the liquid has a viscosity that is comparable to the viscosity of an aqueous liquid.

In another aspect of the invention, a disposable cartridge for use with an electronic device for producing an aerosol for inhalation by a person comprises: a liquid container containing a liquid which when aerosolized is intended for inhalation by a person; and a transducer that, when actuated, causes the liquid from the container to be aerosolized such that the aerosol may be inhaled by a person; wherein the liquid comprises an active agent entrapped by liposomes. In this respect, the liquid is considered to be a liquid mixture.

In a feature, the active agent comprises nicotine.

In a feature, the active agent comprises tetrahydrocannabinol.

In a feature, the active agent comprises cannabidiol.

In a feature, the liquid comprises nanoparticles formed by an oil droplet covered by a monolayer of phosphatidylcholine.

In another aspect, a disposable cartridge for use with an electronic device for producing an aerosol for inhalation by a person comprises: a liquid container containing a liquid mixture comprising a nanodispersion which when aerosolized is intended for inhalation by a person; and a transducer that, when actuated, causes the liquid mixture from the container to be aerosolized such that the aerosol may be inhaled by a person.

In a related aspect of the invention, an electronic device for producing an aerosol for inhalation by a person comprises: a mouthpiece and an upper housing component to which the mouthpiece attaches, wherein the upper housing component contains a container and a mesh assembly having a mesh material that vibrates when actuated for aerosolizing a liquid contained in the container that comes into contact with the vibrating mesh material, and wherein the aerosol so produced may be inhaled through the mouthpiece; and a lower housing component containing circuitry and a power supply for actuating vibration of the mesh material, wherein electrical pathways connect the mesh assembly of the upper housing component with the circuitry and power supply of the lower housing component.

In a feature of this aspect, the upper housing component and the lower housing component are detachable from each other, and electrical contacts connect the electrical pathways between the upper housing component and the lower housing component when the upper housing component and the lower housing component are connected.

In another feature, the mouthpiece is detachable from the upper housing component to expose the vibrating mesh material. In this respect, the mouthpiece preferably snaps onto a rim surrounding a recessed area or opening of the upper housing component in which the vibrating mesh material is located, thereby defining a partially enclosed space above the vibrating mesh material.

In a feature, the device comprises no heating element configured to heat the liquid to aerosolize the liquid.

In a feature, the device comprises no compressed gas configured to aerosolize the liquid.

In a feature, the electronic device produces a fine particle, low velocity aerosol for central and deep lung deposition.

In a feature, the mesh assembly comprises an oscillating piezoelectric material that when actuated results in vibrations of the mesh material, which aerosolizes a liquid that comes into contact with one side thereof, the aerosol being produced on the opposite side of the vibrating mesh material in the partially enclosed space defined by the mouthpiece when attached to the upper housing component. The oscillating piezoelectric material may be a single layer oscillating piezoelectric material, or the oscillating piezoelectric material may be a multi-layer oscillating piezoelectric material. The oscillating piezoelectric material preferably forms part of a piezo mesh disk.

In a feature, the liquid is pressured into contact with a first side of the vibrating mesh material, and the vibrating mesh material comprises small openings through which droplets of the liquid pass to form the aerosol as the vibrating mesh material oscillates. Furthermore, the droplets of the aerosol produced preferably are between one-micron and four-micron aerosol droplets.

In a feature, the container comprises a cartridge.

In a feature, the power supply comprises one or more lithium-ion batteries.

In a feature, the power supply comprises one or more rechargeable batteries.

In a feature, the circuitry and power supply are configured to further operate a pump system that causes the liquid from the container to come into contact with the first side of the vibrating mesh material. The pump system preferably comprises a motor and a threaded shaft that is rotated by the motor, the rotation of the threaded shaft causing the liquid to be pushed toward the vibrating mesh material. The liquid preferably is pushed toward the vibrating mesh material by a stopper that is advanced by the rotating shaft; the stopper is advanced by engagement with a plunger that is attached to the threaded shaft and that is directly driven by rotation of the threaded shaft by the motor, or alternatively, the stopper is attached to the threaded shaft and is directly driven by rotation of the threaded shaft by the motor.

In another feature, the electronic device further comprises means for causing the liquid to be in contact with a lower side of the mesh material facing the container. The means may comprise any of the pump systems disclosed herein, whether actively powered or a passive system, such as a capillary pump. The means further may comprise a stopper. In another feature, the electronic device comprises a capillary pump, wherein the liquid is drawn into contact with the mesh material through capillary action.

In another feature, the upper housing component and the lower housing component fit together to define a body of the electronic device, which body is of a size and shape for gripping and holding by hand during use of the electronic device.

In another related aspect, an electronic device for producing an aerosol for inhalation by a person comprises: (a) a mouthpiece; and (b) an elongate housing having opposite first and second ends, with the mouthpiece being attached to the first end and with the housing comprising therein, (i) a mesh assembly comprising a mesh material that vibrates when actuated, (ii) a liquid container containing a liquid that is aerosolized by the mesh material when actuated for inhalation through the mouthpiece, and (iii) circuitry and a power supply for actuating vibration of the mesh material, wherein electrical pathways connect the mesh assembly with the circuitry and power supply; (c) wherein the mesh assembly and the container are arranged in-line along a longitudinal axis of the electronic device.

In a feature, the mesh assembly extends between and separates the mouthpiece and the container.

In a feature, the power supply of the electronic device comprises batteries that are arranged along the longitudinal axis of the device and that are located at the second end of the housing.

In a feature, the liquid contacts the mesh material as a result of capillary action.

In a feature, the electronic device further comprises means for causing the liquid to be in contact with a lower side of the mesh material facing the container.

In another related aspect, a method for producing an aerosol for inhalation by a person using an electronic device comprises the steps of causing a mesh material to vibrate while causing a liquid to contact a first side of the mesh material, whereby droplets of the liquid are formed on the opposite side of the mesh material to create an aerosol for inhalation.

In a feature, the mesh assembly comprises a piezo mesh disk and the liquid is caused to contact the first side of the piezo mesh disk at a generally constant pressure so that the aerosol that is produced will have a generally consistent concentration of the liquid. Additionally, the liquid preferably is maintained in constant contact with the first side of the piezo mesh disk, even when not actuated. Additionally, the electronic device preferably is actuated for a predetermined period of time by a button press, whereby a consistent volume of aerosol for inhalation is produced for each button press. Alternatively, the electronic device is actuated by depressing a button by a person of the electronic device, with the aerosol being produced while the button is depressed. The liquid may be pushed from a cartridge by a stopper that is advanced through a container of the cartridge, and the container of the cartridge may be cylindrical. Furthermore, the stopper may be advanced through the container by actuation of a motor that drives a threaded shaft. This may be accomplished by the stopper being attached to the threaded shaft such that the stopper advances through the container when the threaded shaft is rotated, or by a plunger (or plunger head) being attached to the threaded shaft and advancing through the container when the threaded shaft is rotated such that the plunger engages and advances the stopper for pushing the liquid into contact with the vibrating mesh material.

In another feature, the aerosol preferably is produced without smoldering of the liquid.

In another feature, the aerosol is produced without utilizing a compressed gas.

In another related aspect, a method for producing an aerosol for inhalation by a person using an electronic device having a mouthpiece comprises the steps of causing a mesh material to vibrate while causing a liquid to contact a first side of the mesh material, whereby droplets of the liquid are formed on a second, opposite side of the mesh material to create the aerosol for inhalation through the mouthpiece.

In a feature, the device has opposite longitudinal ends and the mouthpiece is located on one of the opposite longitudinal ends of the device.

In a feature, the mesh material has a side facing the mouthpiece and an opposite side facing a container containing the liquid for aerosolized.

In a feature, the mouthpiece, the mesh material, and the liquid container are arranged in-line along the longitudinal axis of the electronic device, with the mesh material extending between and separating the mouthpiece from the liquid container. The mesh assembly in some preferred embodiments comprises a piezo mesh disk.

In a feature, the electronic device is actuated for a predetermined period of time for producing a consistent volume of aerosol for inhalation.

In a feature, the electronic device is actuated by depressing a button by a person of the electronic device.

In a feature, the liquid is caused to contact the first side of the mesh material at a generally constant pressure.

In a feature, the liquid is pushed from a cartridge by a stopper that is advanced through a liquid container of the cartridge. The container of the cartridge preferably is cylindrical but may have another geometric profile. The stopper preferably is advanced through the container by actuation of a motor that drives a shaft. The stopper may be attached to the shaft and directly driven so as to advance through the container when the shaft is rotated, or the electronic device may further comprise a plunger is attached to the shaft and that is directly driven so as to advance through the container when the shaft is rotated, wherein the plunger engages and advances the stopper for pushing the liquid into contact with the vibrating mesh material.

In a feature, the aerosol preferably is produced without smoldering of the liquid.

In a feature, the aerosol preferably is produced without utilizing a compressed gas.

In a feature, the method further comprises a step for causing the liquid to be in constant contact with the mesh material using capillary action. The step may be carried out by an active pump system or a passive pump system such as a capillary pump system using capillary action.

Additional aspects and features of the invention are set forth in the incorporated priority documents and in the applicant's copending patent application Ser. No. 16/548,831 filed on Aug. 22, 2019, which application, and any publication thereof and any patent issuing therefrom, each is incorporated herein by reference.

Another aspect comprises using an electronic device in accordance with one or more of the aforementioned aspects and features to perform a method of producing an aerosol for inhalation by a person using such electronic device.

In addition to the aforementioned aspects and features of the invention, it should be noted that the invention further encompasses the various logical combinations and subcombinations of such aspects and features. Thus, for example, claims in this or a divisional or continuing patent application or applications may be separately directed to any aspect, feature, or embodiment disclosed herein, or combination thereof, without requiring any other aspect, feature, or embodiment.

BRIEF DESCRIPTION OF THE DRAWINGS

One or more preferred embodiments of the invention now will be described in detail with reference to the accompanying drawings, wherein the same elements are referred to with the same reference numerals.

FIG. 15 is a block diagram of a method for producing a fine particle, low velocity aerosol using a preferred electronic device in accordance with one or more aspects and features of the invention.

DETAILED DESCRIPTION

Figure 1:
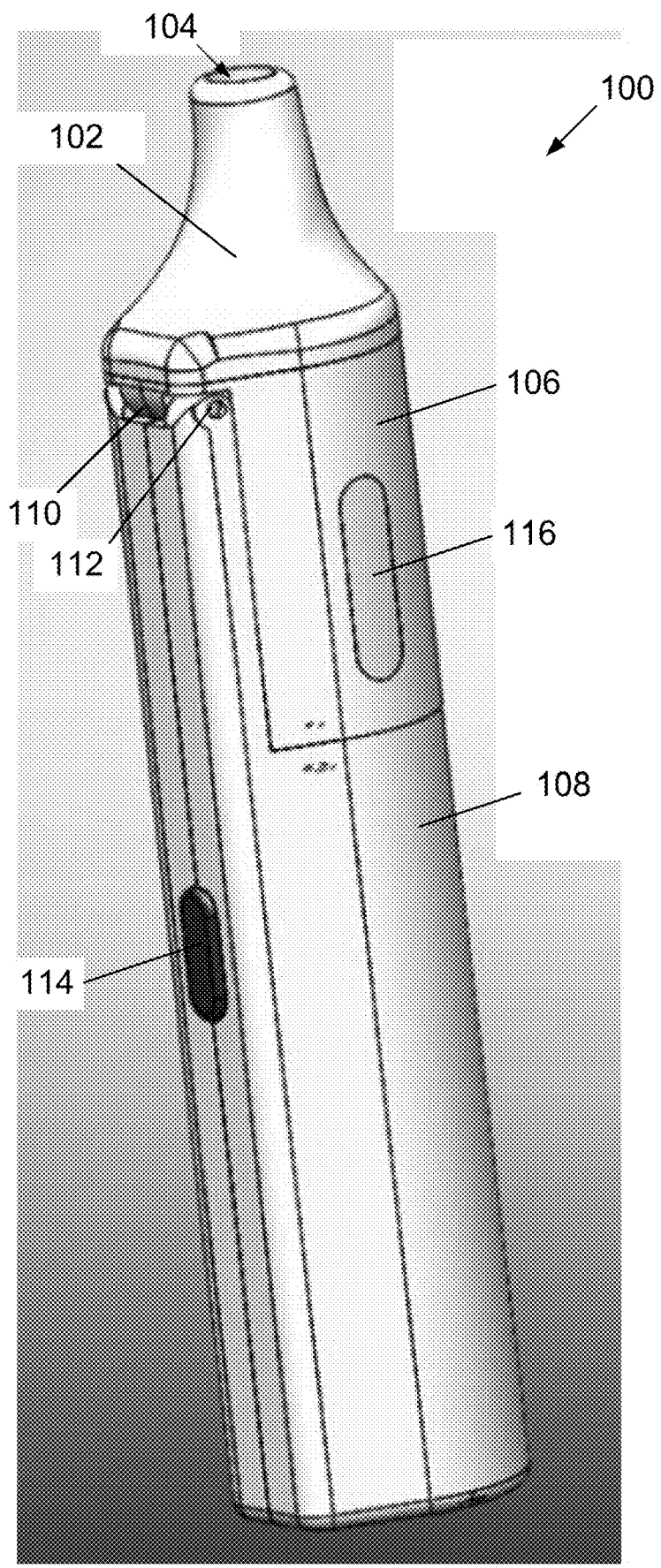
FIG. 1 is a perspective view of a preferred electronic device in accordance with one or more aspects and features of the invention.

As a preliminary matter, it will readily be understood by one having ordinary skill in the relevant art ("Ordinary Artisan") that the invention has broad utility and application. Furthermore, any embodiment discussed and identified as being "preferred" is considered to be part of a best mode contemplated for carrying out the invention. Other embodiments also may be discussed for additional illustrative purposes in providing a full and enabling disclosure of the invention. Furthermore, an embodiment of the invention may incorporate only one or a plurality of the aspects of the invention disclosed herein; only one or a plurality of the features disclosed herein; or combination thereof. As such, many embodiments are implicitly disclosed herein and fall within the scope of what is regarded as the invention.

Accordingly, while the invention is described herein in detail in relation to one or more embodiments, it is to be understood that this disclosure is illustrative and exemplary of the invention and is made merely for the purposes of providing a full and enabling disclosure of the invention. The detailed disclosure herein of one or more embodiments is not intended, nor is to be construed, to limit the scope of patent protection afforded the invention in any claim of a patent issuing here from, which scope is to be defined by the claims and the equivalents thereof. It is not intended that the scope of patent protection afforded the invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the invention. Accordingly, it is intended that the scope of patent protection afforded the invention be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

With regard to the construction of the scope of any claim in the United States, no claim element is to be interpreted under 35 U.S.C. 112(f) unless the explicit phrase "means for" or "step for" is actually used in such claim element, whereupon this statutory provision is intended to and should apply in the interpretation of such claim element. With regard to any method claim including a condition precedent step, such method requires the condition precedent to be met and the step to be performed at least once but not necessarily every time during performance of the claimed method.

Furthermore, it is important to note that, as used herein, "comprising" is open-ended insofar as that which follows such term is not exclusive. Additionally, "a" and "an" each generally denotes "at least one" but does not exclude a plurality unless the contextual use dictates otherwise. Thus, reference to "a picnic basket having an apple" is the same as "a picnic basket comprising an apple" and "a picnic basket including an apple", each of which identically describes "a picnic basket having at least one apple" as well as "a picnic basket having apples"; the picnic basket further may contain one or more other items beside an apple. In contrast, reference to "a picnic basket having a single apple" describes "a picnic basket having only one apple"; the picnic basket further may contain one or more other items beside an apple. In contrast, "a picnic basket consisting of an apple" has only a single item contained therein, i.e., one apple; the picnic basket contains no other item.

When used herein to join a list of items, "or" denotes "at least one of the items" but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers"; the picnic basket further may contain one or more other items beside cheese and crackers.

When used herein to join a list of items, "and" denotes "all of the items of the list". Thus, reference to "a picnic basket having cheese and crackers" describes "a picnic basket having cheese, wherein the picnic basket further has crackers", as well as describes "a picnic basket having crackers, wherein the picnic basket further has cheese"; the picnic basket further may contain one or more other items beside cheese and crackers.

The phrase "at least one" followed by a list of items joined by "and" denotes an item of the list but does not require every item of the list. Thus, "at least one of an apple and an orange" encompasses the following mutually exclusive scenarios: there is an apple but no orange; there is an orange but no apple; and there is both an apple and an orange. In these scenarios if there is an apple, there may be more than one apple, and if there is an orange, there may be more than one orange. Moreover, the phrase "one or more" followed by a list of items joined by "and" is the equivalent of "at least one" followed by the list of items joined by "and".

Referring now to the drawings, one or more preferred embodiments of the invention are next described. The following description of one or more preferred embodiments is merely exemplary in nature and is in no way intended to limit the invention, its implementations, or uses.

In accordance with electronic devices of the invention, a vibrating mesh is provided for aerosolizing a liquid without smoldering. The aerosolized liquid preferably is in the form of a vapor cloud similar to what a person or observer would surmise to be "vapor" when vaping. In the context of vaping, such preferred devices of the invention therefore are believed to produce an aerosol that is carcinogen free. This is in stark contrast to vaporizers used today to aerosolize e-liquids by heating the e-liquids and desired compounds contained therein (e.g., nicotine) or supplements such as B12, THC/CBD and other drugs or stimulants. As a result of using heating to aerosolize the e-liquids, these vaporizers produce toxic byproducts like formaldehyde, a recognized Group 1 carcinogen for caner, which toxic byproducts then are unfortunately inhaled by a person using the vaporizer. For example, when the liquids are heated, the liquids undergo a thermochemical reaction producing unwanted emissions. The unwanted emissions of the toxic byproducts may cause bodily harm from extended inhalation exposure.

By utilizing a vibrating mesh, preferred electronic devices in accordance with one or more aspects and features of the invention produce an aerosol without using heat and thus advantageously avoid such toxic byproducts created by the vaporizes currently on the market. The electronic devices thereby advantageously produce a carcinogen free aerosol free of harmful emission byproducts.

One of the primary performance metrics evaluated for aerosols is the residual aerodynamic particle size distribution ("APSD") of the aerosolized drug product. The residual APSD is characterized by the residual mass median aerodynamic diameter ("MMAD") and the geometric standard deviation ("GSD"). The MMAD signifies the aerodynamic diameter at which half of the aerosolized drug mass lies below the stated diameter.

The $MMADR=MMDI \times pI \times CNV^{1/3} \times pR^{1/6}$, where MMADR (μm) 1s the mass median aerodynamic diameter of the residual particles, MMDI (μm) is the mass median diameter (MMD) of the initial droplets, CNV (weight fraction) is the concentration of the non-volatile components (e.g., dissolved drug and excipients) in the formulation, and pI and pR are the densities (g/cm3) of the formulation and the residual particles, respectively.

The vibrating mesh may be configured and arranged to produce an aerosol for various applications. For example, the arrangement and geometry of various features of the vibrating mesh, such as the design of the vibrating mesh and more specifically the design of the aperture holes of the vibrating mesh, may be adapted to produce an aerosol with various particle sizes, flow properties, and fine particle fractions. The size (e.g., diameter), shape (e.g., oval, circular, triangular, etc.), spacing (e.g., distance between aperture holes, aperture hole density), etc. of the aperture holes may be configured and modified to adjust the size of the aerosol particles for specific applications. Additionally, the thickness of the mesh, especially when in the form of a plate, may also be configured to optimize aerosol properties. For example, the thickness of the plate may impart different properties and characteristics to the aerosol. Depending on the thickness of the plate, the holes may taper with a chamfer such that the entrance and/or exit diameter is larger than the bore diameter of the aperture hole. In another example, the aperture holes may have a constant diameter without a taper.

In another example, the rigidity of the mesh assembly may be configured to prevent oscillations of varying amplitude across the surface of the mesh, which could result in inconsistent aerosolization performance. For example, the thickness, geometry, and material selection for the vibrating mesh material may enhance the rigidity to prevent unwanted oscillations thereof. In some embodiments, the mesh material may be constructed from a metal alloy, to provide adequate rigidity, mass, durability and inert chemical properties for the aerosolization of different drug formulations. Indeed, the design and dimensions of the mesh material may be selected to optimize the device based on the intended application or use case. For example, the vibrating mesh may be configured to adjust the MMADR, fine particle fraction, air/particle velocity, etc. Additionally, the mesh material may also determine the resulting particle properties such as volume diameter, bulk density, tap density, shape, charge, etc.

In addition to the mechanical aspects of the mesh material and its operation, it is believed that the material substrate from which the mesh is constructed and the way in which the holes are generated have important implications for the aerosolization of different drug formulations. In some embodiments, the aperture holes may be electro formed or laser formed. It should be appreciated that other manufacturing methods may be used to form the aperture holes. Example methods for mesh production include electroplating and laser cutting, which may be used to produce a tapered hole. A tapered hole may optimize mesh performance by amplifying flow at the nozzle while reducing viscose losses. The electroplating method makes use of a lithographic plate and the eventual size of the mesh holes may be determined by the duration of the electroplating process. The holes become smaller as the metal is deposited on the edge of the hole over time. Laser cutting involves the use of a laser beam to cut the mesh holes into a thin sheet of metal or polymer material. Laser cutting metal may result in molten material being deposited around the hole, which may be removed by polishing.

In some embodiments, the liquid delivery system may be adapted for a specific liquid. For example, viscosity may be a controlling variable in the size of the aperture holes of the vibrating mesh. Some preferred liquids comprise nicotine, which is less viscous than a cannabinoid derivative (e.g., tetrahydrocannabinol ("THC") and cannabidiol ("CBD")), which has a higher viscosity. Other considerations may include water solubility, surface tension, acidity and/or basicity, and whether the liquid contains a liquid carrier. Some preferred liquids indeed comprise liquid carriers and, in particular, liposomal carriers. Various liquids and formulations may be used to form aerosols from electronic devices of the invention. These formulations may have widely different physiochemical properties, such as surface tension, density, viscosity, characteristics of intramolecular forces within the formulation and whether the formulation is a pure liquid or a suspension of particles within a liquid. Each of the above-mentioned physiochemical properties may affect the functionality, consistency, efficacy, and end properties of the resulting aerosol or vapor cloud.

The liquid delivery system also may be designed to provide different flow rates. For example, the pump may be an active pump or a passive pump. Additionally, in some preferred embodiments the output rate, pressure supplied by the pump, or both, may be adjusted to provide different flow rates.

In some embodiments, the geometry of the mesh may be the form of a dome-like structure. In some embodiments, the mesh may be flat and may be in the form of a plate. Other orientations and geometries also are contemplated within the scope of the invention.

Figure 22:
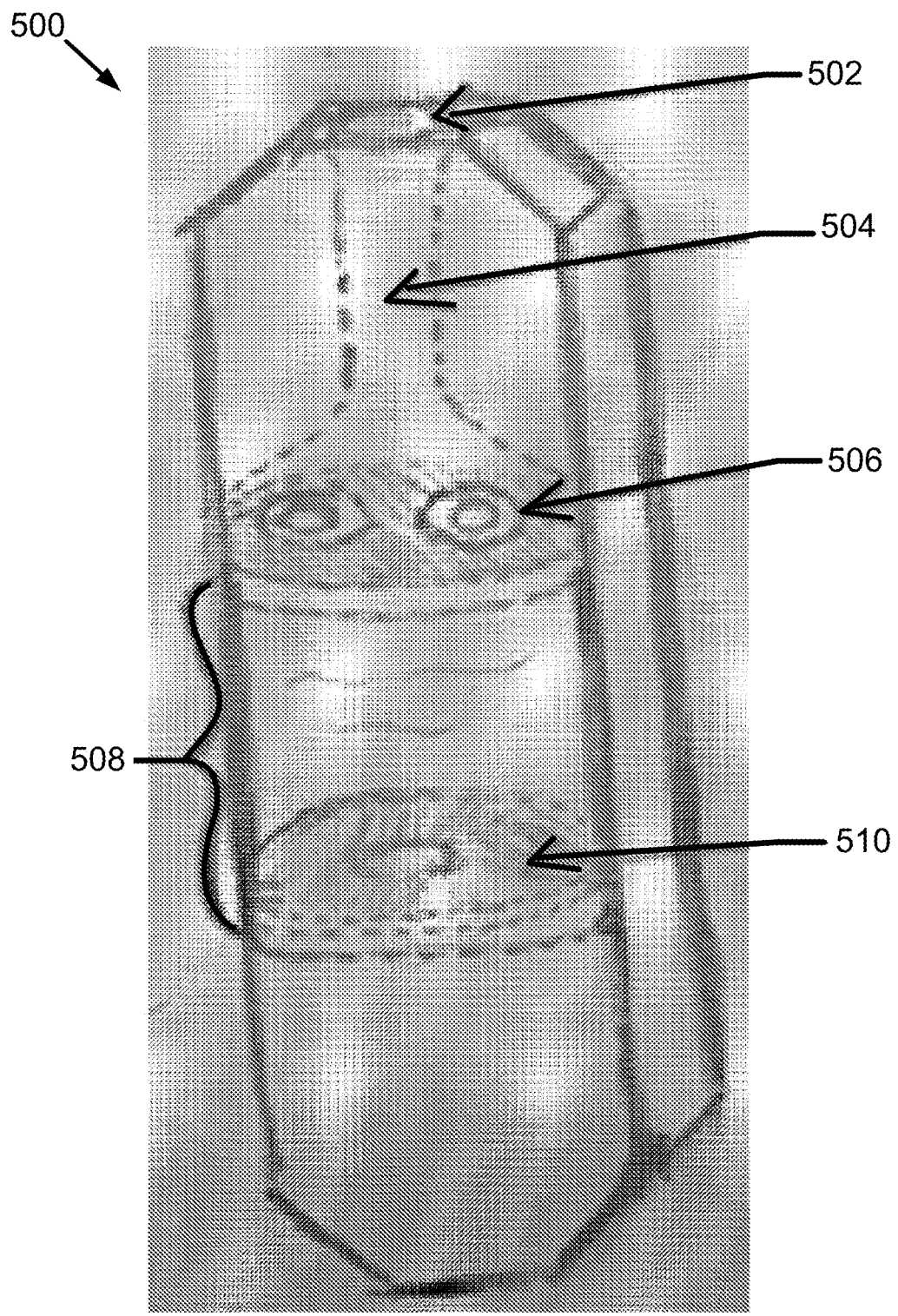
FIG. 22 is an internal schematic illustration of the preferred electronic device of FIG. 21, wherein the outer housing is rendered transparent in the figure for illustration.
Figure 24:
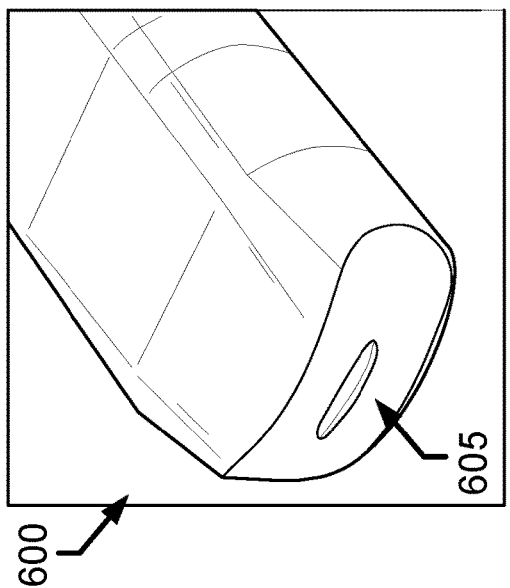
FIG. 24 is a partial perspective view of an ultrasonic device corresponding to the ultrasonic device schematically represented in FIG. 23.
Figure 23:
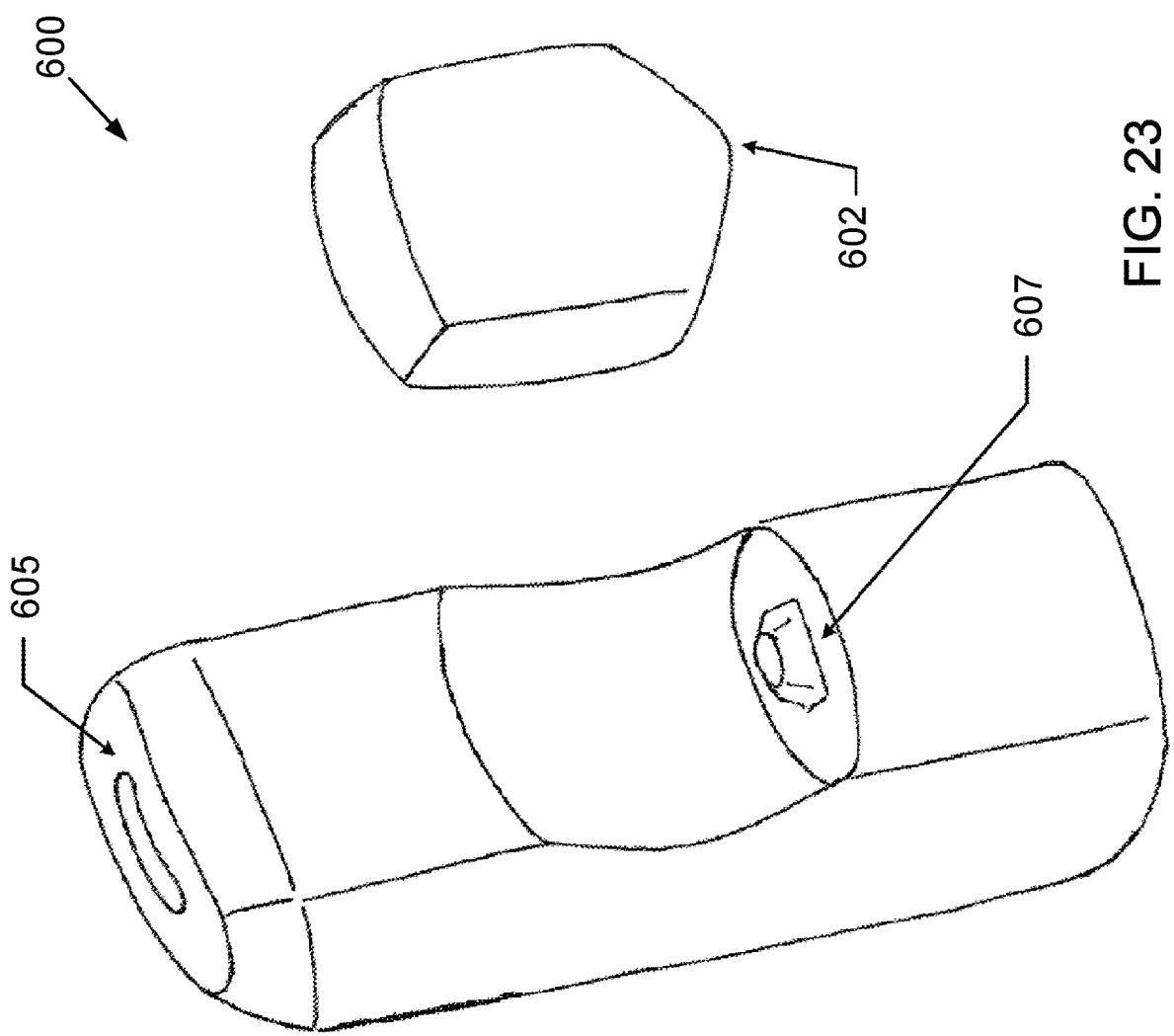
FIG. 23 is a schematic perspective view of a preferred electronic device comprising an ultrasonic nebulizer with removable cartridge in accordance with one or more aspects and features of the invention.

Additionally, in electronic devices of the invention, the vibrating mesh assembly may include a single layer oscillating piezoelectric material to aerosolize the liquid. In an example, the mesh assembly may have a double or multi-layer structure, and multiple mesh membranes may be arranged to induce an optimum MMAD and/or APSD for the aerosolized liquid. A plurality of vibrating meshes also may be used in the mesh assembly in some embodiments; FIG. 22 for example illustrates a mesh assembly that includes two separate vibrating meshes spaced apart from one another.

Additionally, the mesh assembly may be constructed from one or more different piezoelectric materials to optimize the MMAD and/or APSD.

Additionally, the arrangement and design of the mesh assembly (e.g., placement of the holes, angstrom size) and hygroscopic effects of the lungs may be considered for optimum deposition and diffusion into the bloodstream.

In some embodiments, the electronic device is configured to create a fine particle low velocity aerosol. The resulting aerosol or vapor cloud may be configured to reduce or soften the potential irritation of the airways and lungs. In some embodiments, the encapsulation techniques may create the ideal person experience. As mentioned above, the lungs have clearance mechanisms to prevent invasion of unwanted airborne particles from entering the body. To ensure that the fine particle, low velocity aerosol that achieves central and deep lung deposition, the electronic device and/or formulation may be adapted such that an aerosol is produced that eludes the lung's various lines of defense.

For example, progressive branching and narrowing of the airways encourage impaction of particles. Larger the particle sizes, greater velocities of incoming air, and more abrupt bend angles of bifurcations and the smaller the airway radius increase the probability of deposition by impaction. In essence, the end person may sense/feel more or less impaction based on the above parameters.

Additionally, the lung has a relative humidity of approximately 99.5%. The addition and removal of water can significantly affect the particle size of a hygroscopic aerosol and thus deposition itself. Drug particles are known to be hygroscopic and grow or shrink in size in high humidity, such as in the lung. A hygroscopic aerosol that is delivered at relatively low temperature and humidity into one of high humidity and temperature may increase in size when inhaled into the lung. For example, the rate of growth may be a function of the initial diameter of the particle. As it relates to size and diameter, particles may be deposited by inertial impaction, gravitational sedimentation or diffusion (Brownian motion) depending on their size. While deposition occurs throughout the airways, inertial impaction usually occurs in the first ten generations of the lung, where air velocity is high and airflow is turbulent.

In the therapeutic/medical environment, most particles larger than 10 micrometers are deposited in the oropharyngeal region with a large amount impacting on the larynx, particularly when the drug is inhaled from devices requiring a high inspiratory flow rate (e.g., as with dry powder inhalers ("DPIs")) or when the drug is dispensed from a device at a high forward velocity. The large particles are subsequently swallowed and contribute minimally, if at all, to the therapeutic response. In the tracheobronchial region, inertial impaction may also play a significant role in the deposition of particles, particularly at bends and airway bifurcations. Deposition by gravitational sedimentation may typically predominate in the last five to six generations of airways (smaller bronchi and bronchioles), where air velocity is low. Due to the low velocity, large volume aerosol that is produced in accordance with preferred embodiments of the invention, the aerosol may be less irritating to a person.

In the alveolar region, air velocity is typically negligible, and thus the contribution to deposition by inertial impaction is typically nonexistent. Particles in this region may have a longer residence time and may be deposited by both sedimentation and diffusion. Particles not deposited during inhalation may be exhaled. Deposition due to sedimentation affects particles down to 0.5 micrometers in diameter, whereas below 0.5 micrometers, the main mechanism for deposition is by diffusion.

Targeting the aerosol to conducting or peripheral airways may be accomplished by altering the particle size of the aerosol and/or the inspiratory flow rate. For example, aerosols with a MMAD of approximately 5 micrometers to 10 micrometers may be deposited in the large conducting airways and oropharyngeal region. Particles ranging from approximately 1 micrometer to 5 micrometers in diameter may be deposited in the small airways and alveoli with more than 50% of the particles having a diameter of three micrometers being deposited in the alveolar region.

In some embodiments, the electronic device includes a piezoelectric crystal that vibrates at a high frequency when electrical current is applied. In some embodiments, the vibration may be in the range of 0.5 to 5.0 MHz_ and more specifically within the range of 1.2 to 2.4 MHz. The vibration of the crystal is transmitted to a transducer horn that is in contact with the liquid to be aerosolized. Vibrations transmitted by the transducer horn cause upward and downward movement of a mesh in the form, for example, of a plate, and the liquid passes through the apertures in the mesh plate to form an aerosol. In some embodiments, the mesh plate consists of a plurality of tapered holes (e.g., 500 holes; 1,000 holes; 6,000 holes). Each tapered hole may have a diameter of approximately 3 micrometers. In other examples, larger or smaller diameters may be appropriate for different liquids or applications. The aperture holes advantageously amplify the vibration of the transducer horn throughout the liquid and reduce the amount of power required to generate the aerosol. For example, using a low frequency of vibration with a mesh plate containing numerous minute holes allows efficient generation of a fine particle mist.

In some embodiments, aqueous liquids may be more suitable to generating an aerosol with electronic devices of the invention when compared to other more viscous liquids. In some embodiments, the aqueous liquids may include ethanol, which itself may be a primary liquid carrier of the liquid.

Additionally, in some preferred embodiments ultrasonicated a liposomal nanoemulsions comprises the liquid carrier of the liquid delivery system. Nanoemulsions may be sonicated where liposomes work as carriers for active agents. In some embodiments, liposomes may be prepared and formed (e.g., by ultrasound) for the entrapment of active agents. In some instances, emulsifiers are added to the liposomal dispersions to stabilize higher amounts of lipids; however, additional emulsifiers may cause a weakening on the barrier affinity of a liquid (e.g., phosphatidylcholine). Nanoparticles (e.g., nanoparticles composed of phosphatidylcholine and lipids) preferably are used to solve this. Thus, in some embodiments, nanoparticles are used that preferably are formed by an oil droplet that is covered by a monolayer of phosphatidylcholine. It is believed that the use of nanoparticles allows formulations which are capable of absorbing more lipids and which remain stable whereby additional emulsifiers may not be needed.

As discussed above, ultrasonication is a method for the production of nanoemulsions and nanodispersions. In some embodiments, an intensive ultrasound supplies the power needed to disperse a liquid phase (dispersed phase) in small droplets in a second phase (continuous phase). In the dispersing zone, imploding cavitation bubbles cause intensive shock waves in the surrounding liquid and result in the formation of liquid jets of high liquid velocity. In order to stabilize the newly formed droplets of the disperse phase against coalescence, emulsifiers (surface active substances, surfactants) and stabilizers are added to the emulsion. As coalescence of the droplets after disruption influences the final droplet size distribution, efficiently stabilizing emulsifiers may be used to maintain the final droplet size distribution at a level that is equal to the distribution immediately after the droplet disruption in the ultrasonic dispersing zone.

Some liposomal dispersions (e.g., those based on unsaturated phosphatidylcholine) may lack in stability against oxidation. The stabilization of the dispersion can be achieved by antioxidants, such as by a complex of vitamins C and E. For example, the entrapment of the essential oil in liposomes may increase the oil stability.

In some embodiments, the vibrating mesh is configured to create a fine particle low velocity aerosol which is well suited for central and deep lung deposition. By producing a fine particle, low velocity aerosol, one or more preferred electronic devices of the invention advantageously can produce an aerosol that is adapted to target small airways in the management of asthma and COPD.

Additionally, some embodiments, a pump system is utilized to pump or push the liquid to be aerosolized into contact with the vibrating mesh whereby droplets of the liquid are created on the other side of the vibrating mesh on the order of 1 to 4 microns. While it is contemplated that a capillary pump may be used (wherein the liquid is drawn into contact with the mesh material through capillary action), electronic devices of the invention also may preferably comprise a pump system that is powered by an electrical power source of the device, such as batteries and, preferably, rechargeable batteries. Such a pump system preferably comprises a piezoelectric motor. In some embodiments, however, an active pump system is not used, and the liquid may be gravity-fed to a vibrating mesh or other vibrating structure. Thus, a gravitational pump may be used in such embodiments. This is particularly contemplated when an electronic device of the invention is used in a generally upright position as a nebulizer for drug delivery. In most preferred embodiments, however, the electronic device is orientation-agnostic and generally works as intended in any orientation relative to the directional forces of gravity.

Turning now to the drawings, FIG. 1 is a perspective view of a preferred electronic device 100 for producing an aerosol for inhalation in accordance with one or more aspects and features of the invention. The electronic device 100 comprises a mouthpiece 102 having an opening 104 through which the aerosol is inhaled; an upper housing component 106; and a lower housing component 108. The mouthpiece 102, upper housing component 106, and lower housing component 108 fit together to define a body of the electronic device 100, which body is of a size and shape for gripping and holding by hand during use of the device 100. When used as intended, the electronic device 100 would be held with the mouthpiece 102 oriented upright or at an inclination to horizontal, or any orientation therebetween. Regardless of the orientation, the device 100 works the same in producing the aerosol for inhalation.

The top housing 106 is attached to the lower housing component 108 via a hinge 110 including hinge pin 112 for pivoting movement of the top housing 106 relative to the bottom housing 108 between an open position and a closed position. The closed position is shown, for example, in FIG. 1. The mouthpiece 102 preferably snaps in friction fit onto the top housing 106.

Figure 17:
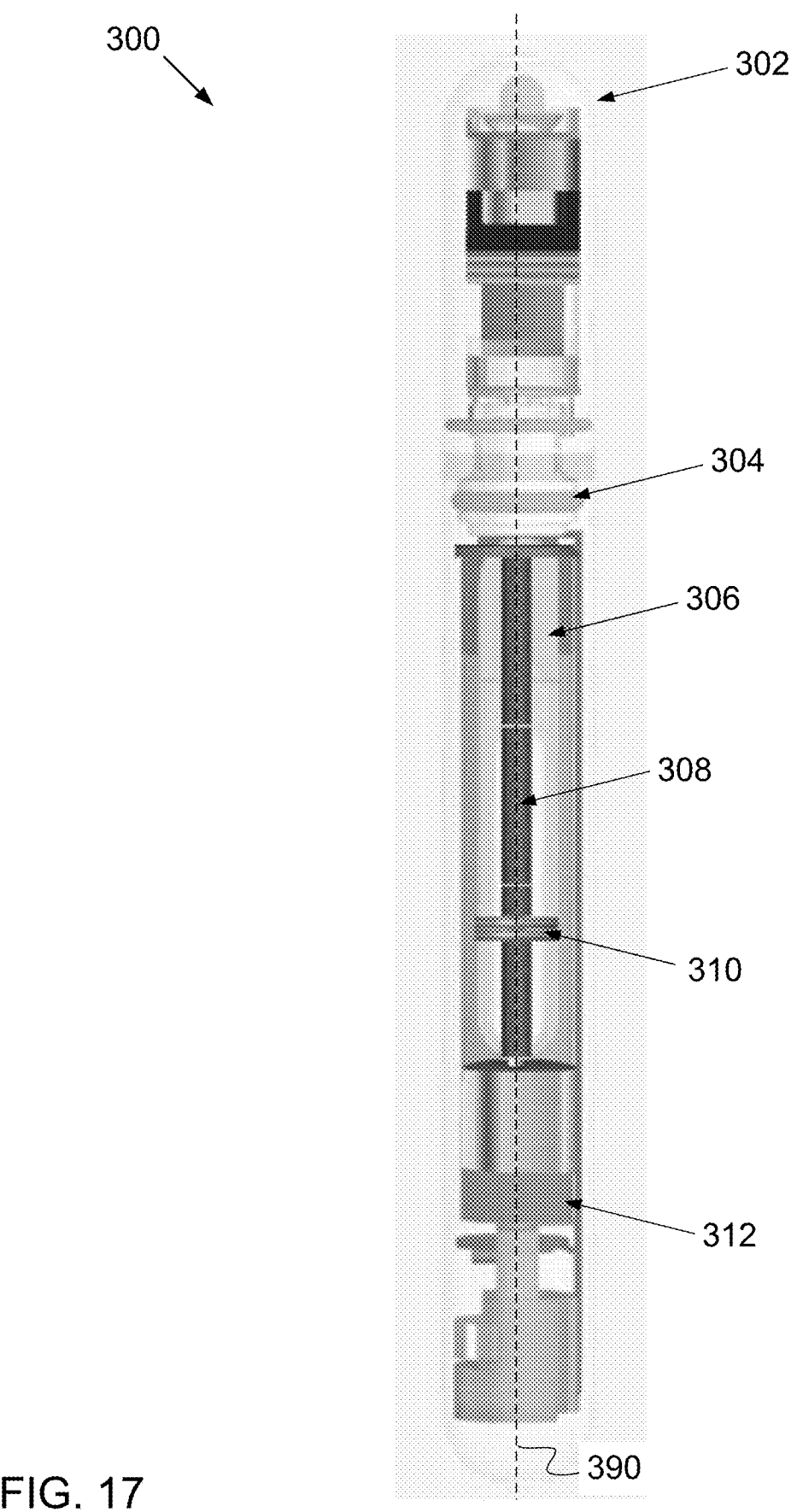
FIG. 17 is a transparent view of internal components of another preferred electronic device in accordance with one or more aspects and features of the invention, wherein the outer housing is rendered transparent in the figure for illustration.

The form factor of the electronic device 100 resembles that of a nebulizer for administering drugs including, for example, prescription medicines. Electronic devices of the invention are not limited to such form factors. For example, another electronic device 300 of the invention is illustrated in FIG. 17, discussed below; electronic device 300 has a form factor resembling that of a vape pen.

Continuing with the description of the electronic device 100, and with further reference to FIG. 1, the device 100 further comprises a button 114 for turning on or otherwise actuating the device 100 and a window 116 for viewing a level of liquid in the device 100. When actuated, the device preferably produces an aerosol for inhalation. A set, predetermined volume of liquid contained in the device preferably is aerosolized each time the device is turned on or actuated using button 114. The amount of liquid remaining in the device to be aerosolized preferably is viewable through the window 116.

Figure 2:
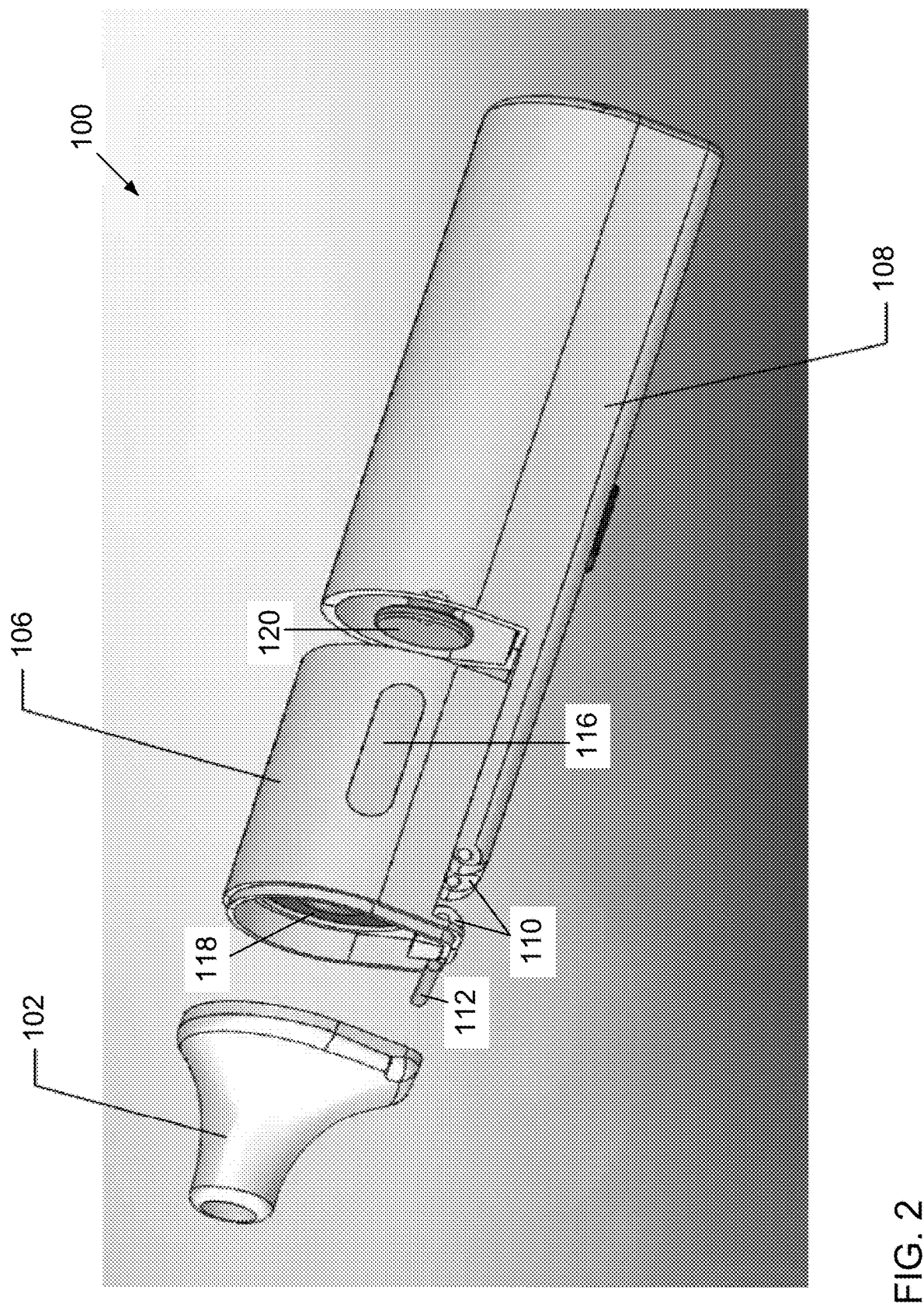
FIG. 2 is an exploded view of components of the electronic device of FIG. 1.

FIG. 2 is an exploded view of components of the electronic device 100. As seen in FIG. 2, the mouthpiece 102, upper housing component 106, and lower housing component 108 are separable from each other. Thus, the body can be disassembled by a person. A glimpse of a mesh assembly 118 including a vibrating mesh in the form of a vibrating mesh material contained within the upper housing component 106 and a glimpse of a plunger 120 contained within the lower housing component 108 also are seen in FIG. 2.

Figure 3:
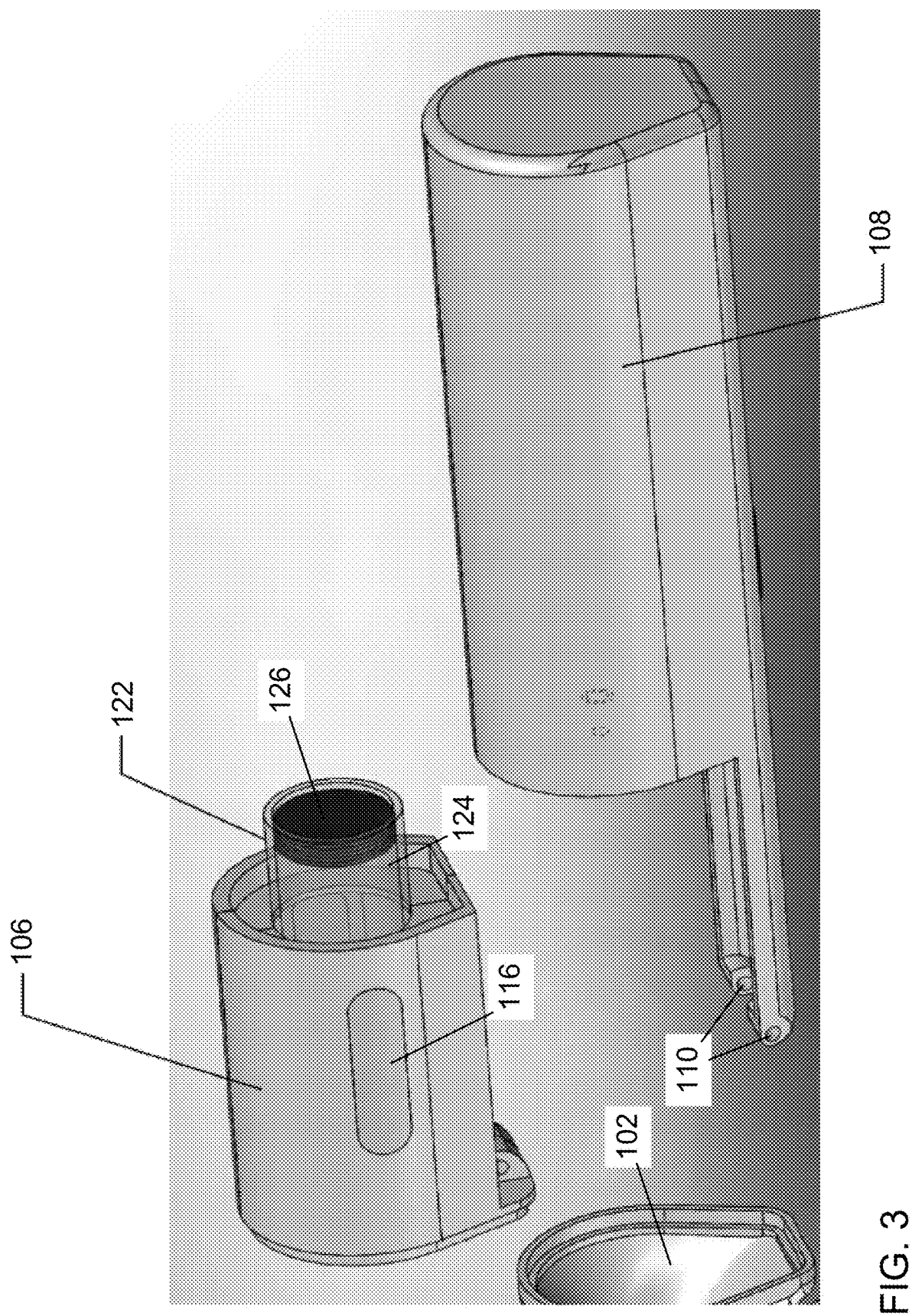
FIG. 3 is another exploded view of components of the electronic device of FIG. 1, wherein component 122 is rendered transparent in the figure for illustration.

FIG. 3 is another exploded view of components of the electronic device 100. FIG. 3 is perhaps best notable for revealing a liquid container for the liquid in the form of a cartridge 122 that is contained within the upper housing component 106. The cartridge 122 contains the liquid that is aerosolized and the cartridge 122 preferably is removable from the upper housing component 106 either when the upper housing component is disconnected and separated from the lower housing component 108 or when the upper housing component 106 is rotated from the closed position to an open position by pivoting around the hinge 110 and hinge pin 112. Preferably following use and depletion the cartridge 122 is replaced with a new cartridge having a full supply of liquid to be aerosolized. The cartridge 122 of FIG. 3 is full of a liquid and is seen being inserted into the upper housing component 106. In alternatives, the container may be a tank, i.e., a refillable container that is intended for multiple uses.

As further seen in FIG. 3, the cartridge 122 comprises a cylinder or barrel 124 and a stopper 126. FIG. 3 further reveals that the upper housing component 106 comprises two windows 116 for viewing the volume of liquid contained within the cartridge during use of the device 100.

Figure 4:
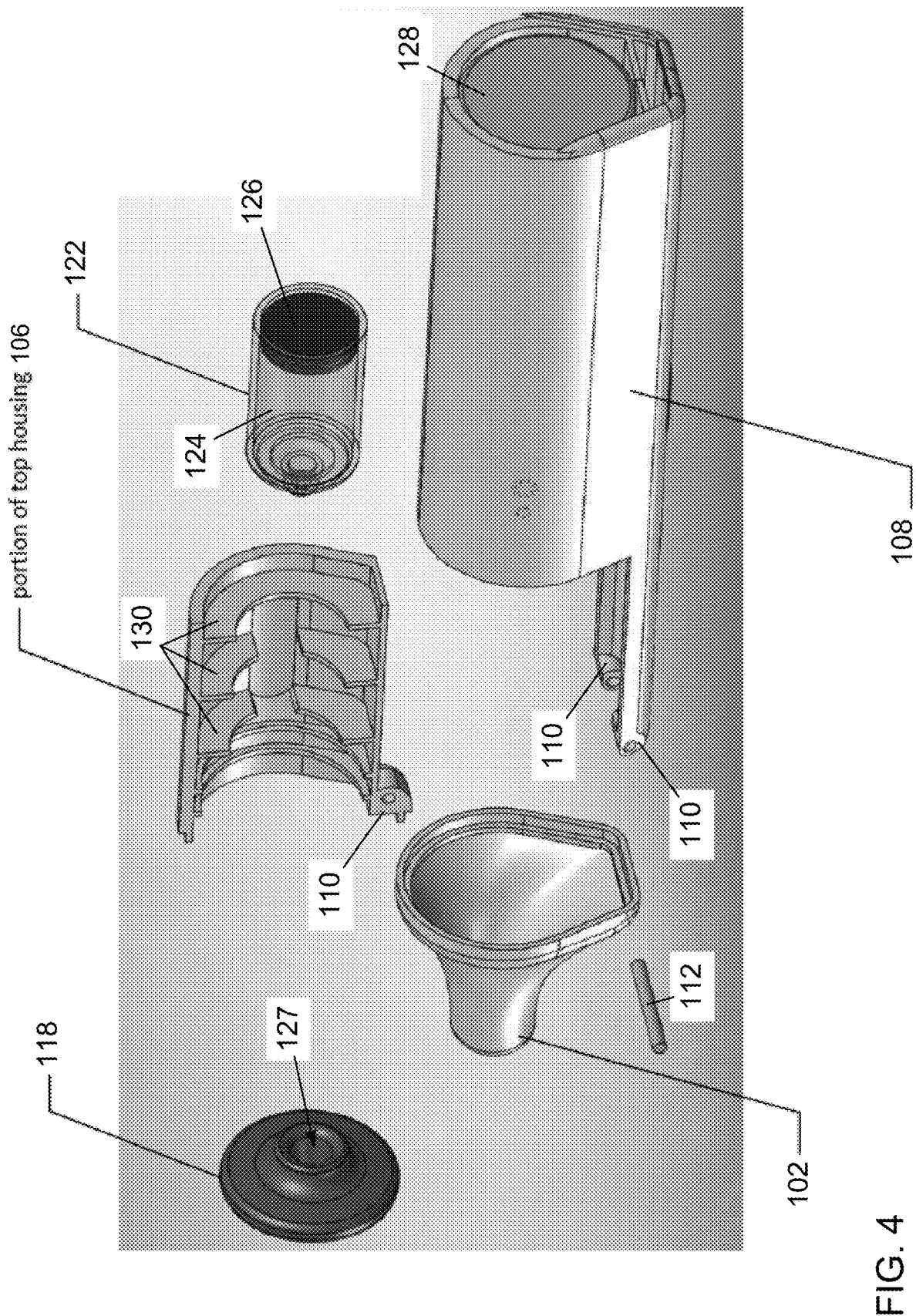
FIG. 4 is a partial, exploded view of components of the electronic device of FIG. 1, wherein component 122 is rendered transparent in the figure for illustration.

FIG. 4 is a partial, exploded view of components of the electronic device 100. FIG. 4 reveals one or more batteries 128 that are contained within a bottom portion of the lower housing component 108. The batteries preferably are rechargeable lithium-ion batteries. The device 100 preferably includes a charging port 140 (illustrated in FIGS. 11-14) for plugging in a power source for charging the batteries 128. The charging port preferably is a micro-USB charging port. FIG. 4 additionally reveals wall supports 130 of the upper housing component 106 which conform to, receive and support in friction fit the cartridge 122 when inserted into the upper housing component 106. The supports 130 preferably are formed as part of the upper housing component 106, such as during an injection molding process of the upper housing component 106. The lower housing component 108 and mouthpiece 102 also preferably are made by injection molding or other manufacturing methodology.

Similar to supports 130, the upper housing component 106 also comprises wall supports 131 (seen for example in FIG. 5) that hold the mesh assembly 118 in place in the upper housing component 106. Supports 131 also preferably form part of the upper housing component 106 and are similarly formed in a molding process.

Figure 5:
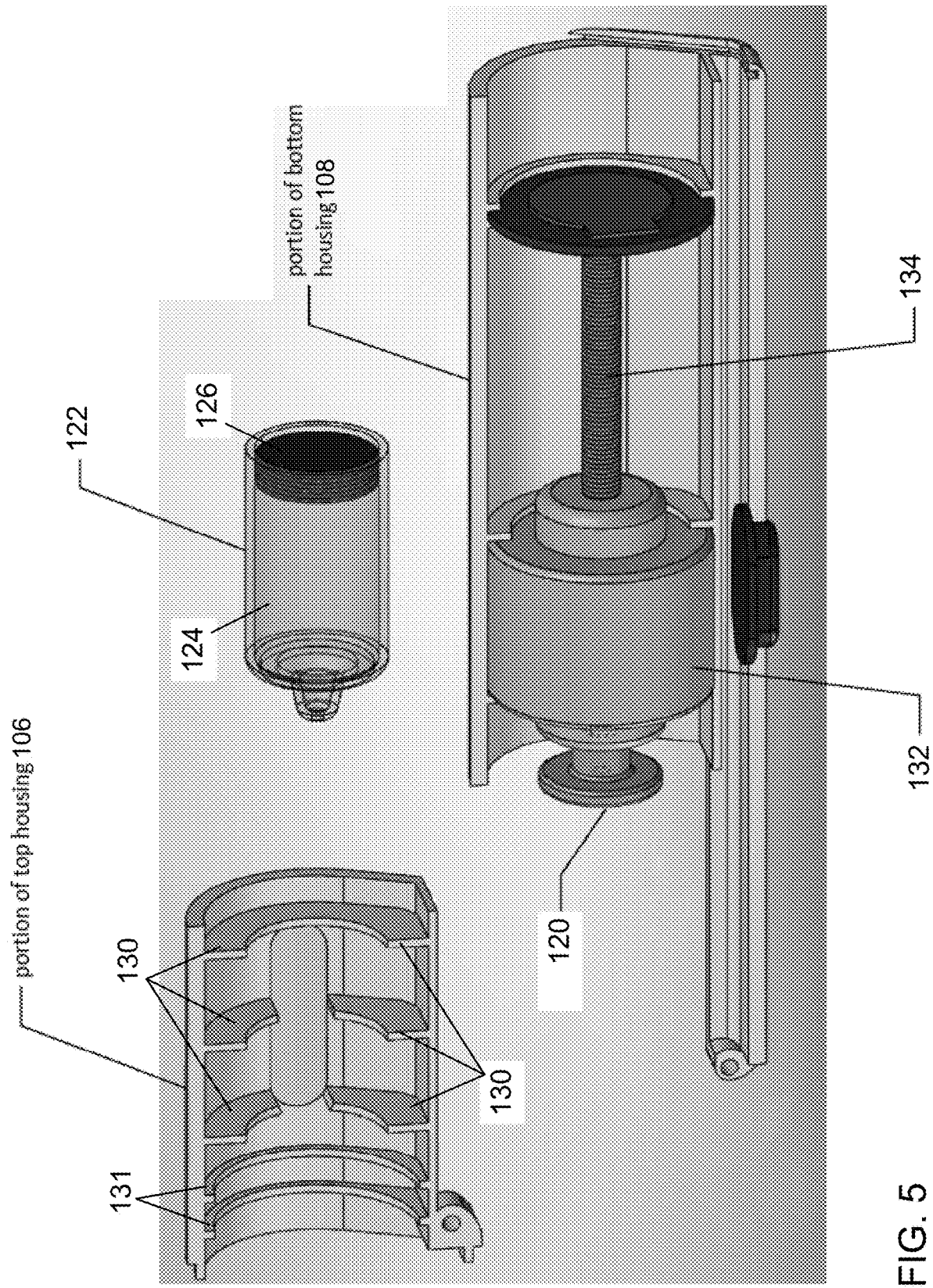
FIG. 5 is another partial exploded view of components of the electronic device of FIG. 1, wherein component 122 is rendered transparent in the figure for illustration.
Figure 6:
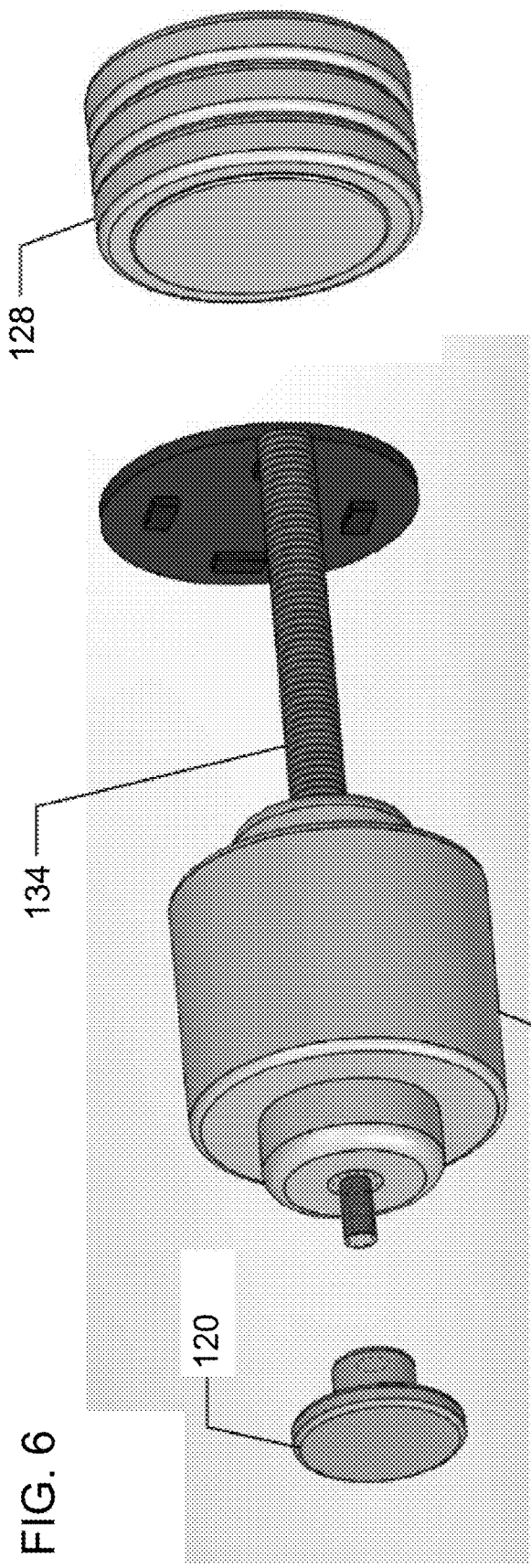
FIG. 6 is another exploded view of components of the electronic device of FIG. 1.
Figure 8:
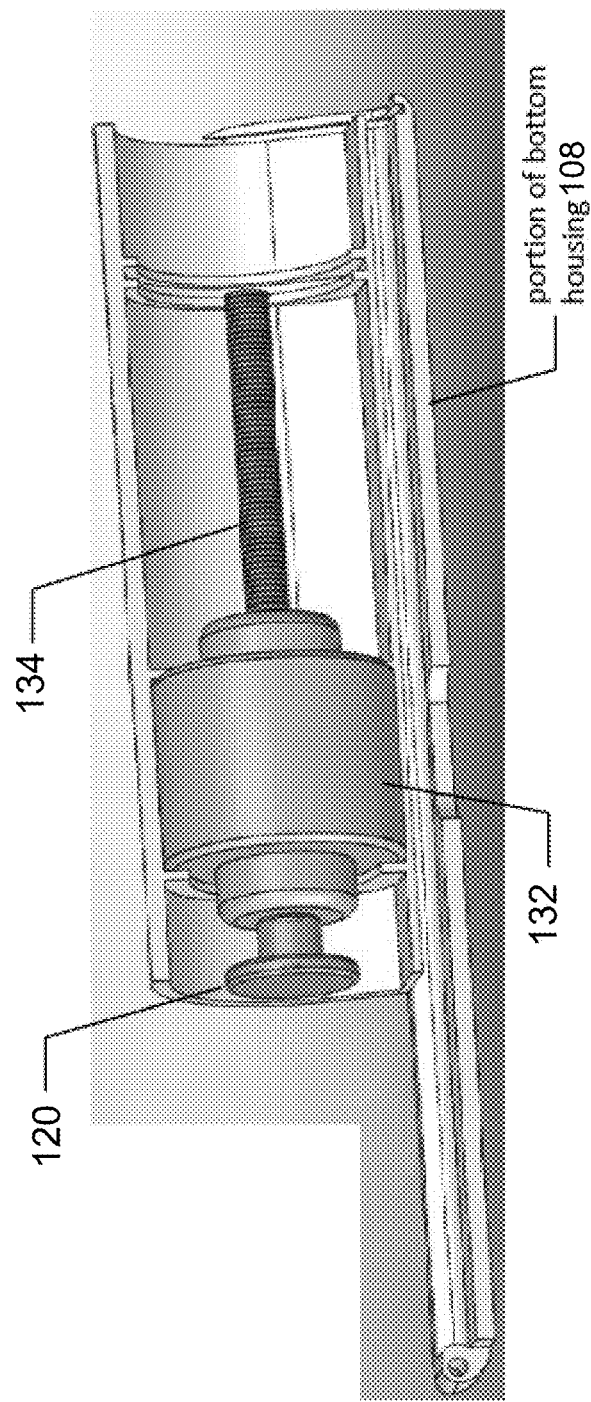
FIG. 8 is a partial view of components of the electronic device of FIG. 1.

FIGS. 5 and 6 each is another partial, exploded view of components of the electronic device 100 and each reveals a motor 132 and threaded shaft 134. The motor 132 preferably is a piezoelectric motor. The motor 132 drives rotation of the threaded shaft 134 and is actuated by the button 114. The plunger 120 is attached to an end of the shaft 134 and rotation of the shaft 134 by the motor 132 causes the plunger to move in a direction parallel to a longitudinal axis of the rotating shaft 134. FIG. 8 is a partial view of components of the electronic device 100 and additionally shows the plunger 120 attached to the end of the threaded shaft 134 and moved to a fully retracted position in which the plunger 120 is located immediate adjacent the motor 132.

In the device 100, the piezoelectric motor 132 preferably utilizes piezoelectric actuation technology using mechanical waves. The motor advantageously provides a high-power density combined with a high efficiency (e.g., greater than 20 W mechanical) for small motors. In some embodiments, the motor is a purely mechanical structure without any winding. An example suitable motor is the piezoelectric motor WLG-30. The motor may have a stator diameter of approximately 30 mm (1.18 inches), a length of approximately 34 mm (1.34 inches), and a height of approximately 15 mm (0.59 inches). The motor may weight approximately 37 g with an electronic card weight of 23 g. In some embodiments, the motor may have a max speed of approximately 300 rpm with a rated torque of approximately 250 mN·m, a max torque of approximately 50 mN·m, a hold torque of approximately 150 mN·m, and a torque reliquid of approximately 0.18 mN·m. Additionally, the motor may have an output power of approximately 150 W. The motor response time may be approximately 1.3 milliseconds with a direction change time (CW/CCW) of approximately 1 millisecond and an angular accuracy of approximately 1 degree. In some embodiments, the motor 132 may have a power supply of approximately 7.5V and a max current of approximately 1.2 A.

Figure 7:
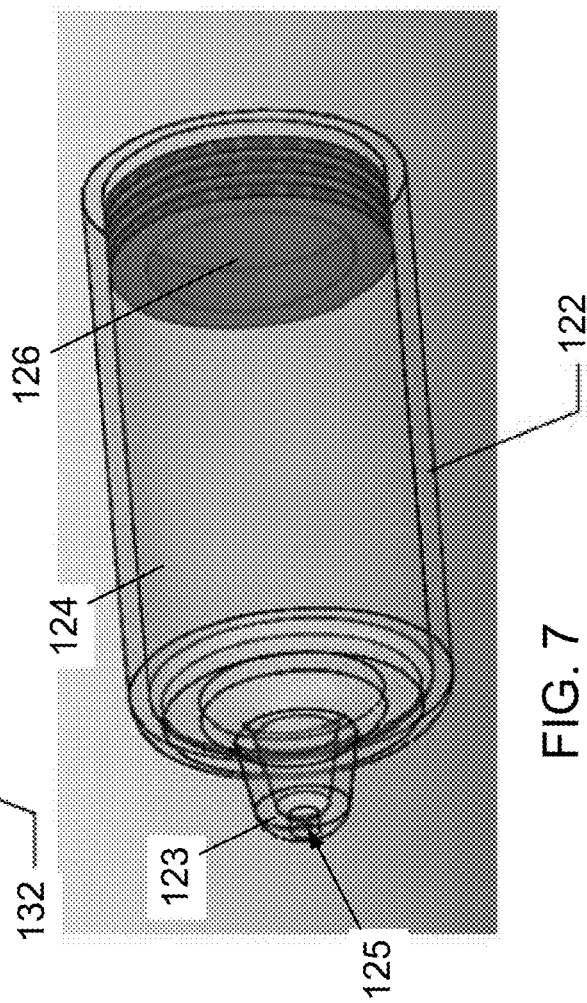
FIG. 7 is a transparent view of components of the electronic device of FIG. 1, wherein component 122 is rendered transparent in the figure for illustration.

FIG. 7 is a transparent view of the cartridge 122 and components thereof in the electronic device 100. The cartridge 122 is similar to a syringe in that the stopper 126, when advanced within the cylinder 124 toward a tapered end 123 of the cartridge 122, pushes liquid in the cylinder 124 toward the tapered end 123. The stopper 126 forms a seal with the cylinder wall 124 and the stopper 126 prevents or stops the liquid from leaking around the stopper 126.

Figure 9:
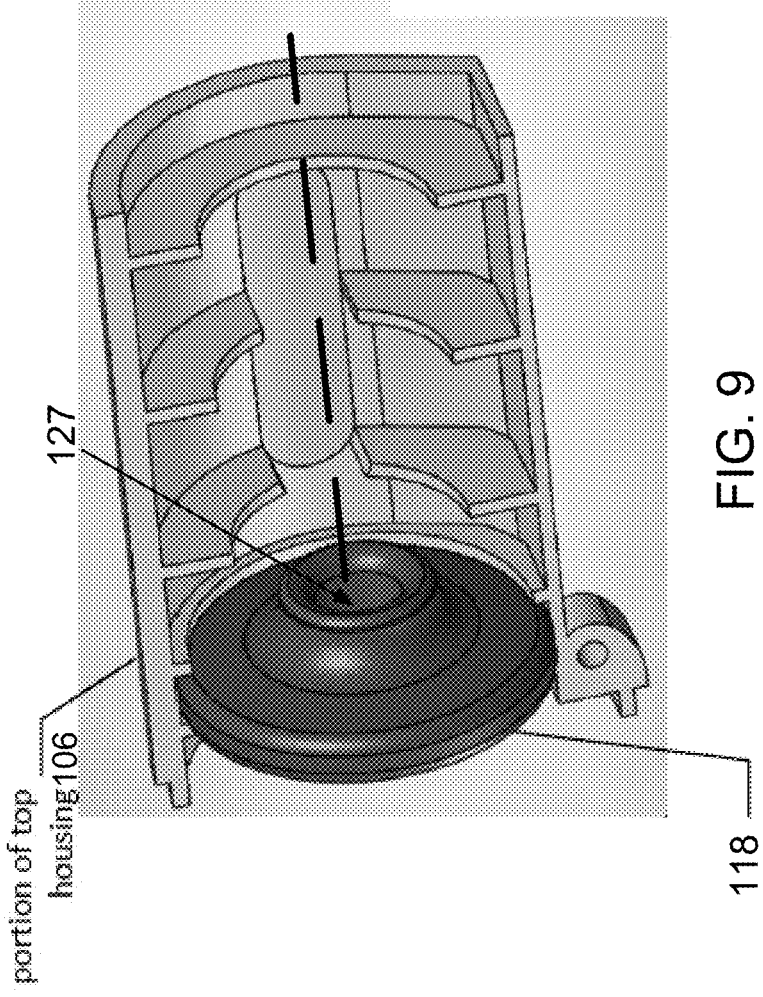
FIG. 9 is another partial view of components of the electronic device of FIG.
Figure 10:
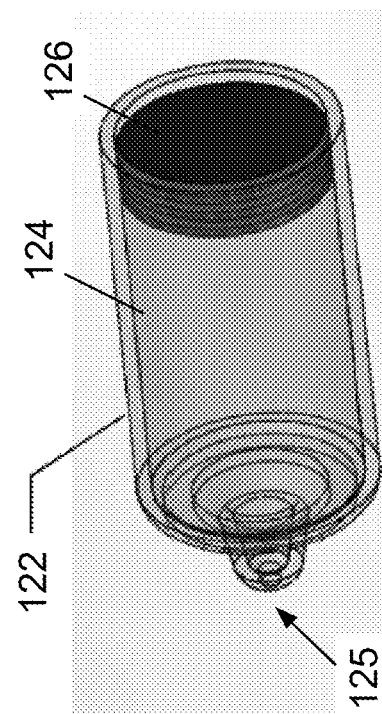
FIG. 10 is a transparent view of the cartridge component of the electronic device of FIG. 1, wherein component 122 is rendered transparent in the figure for illustration.
Figure 11:
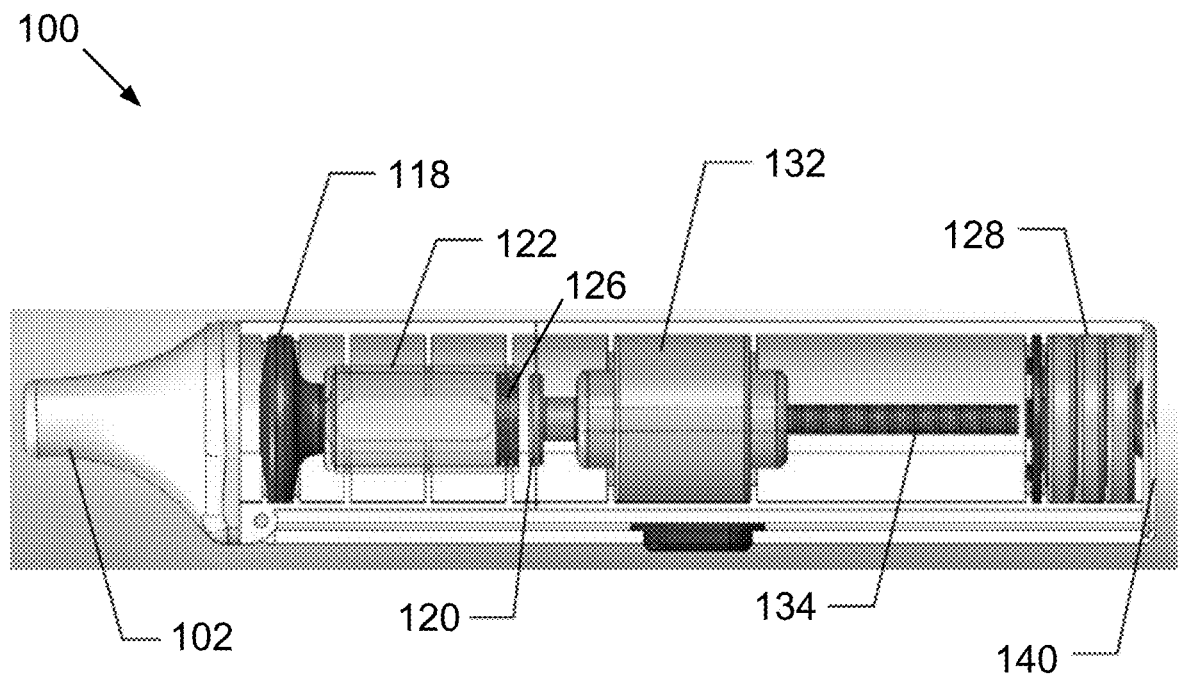
FIGS. 11, 12, 13, and 14 are partially transparent, internal views of the electronic device of FIG. 1, wherein component 122 is rendered transparent in each figure for illustration.
Figure 12:
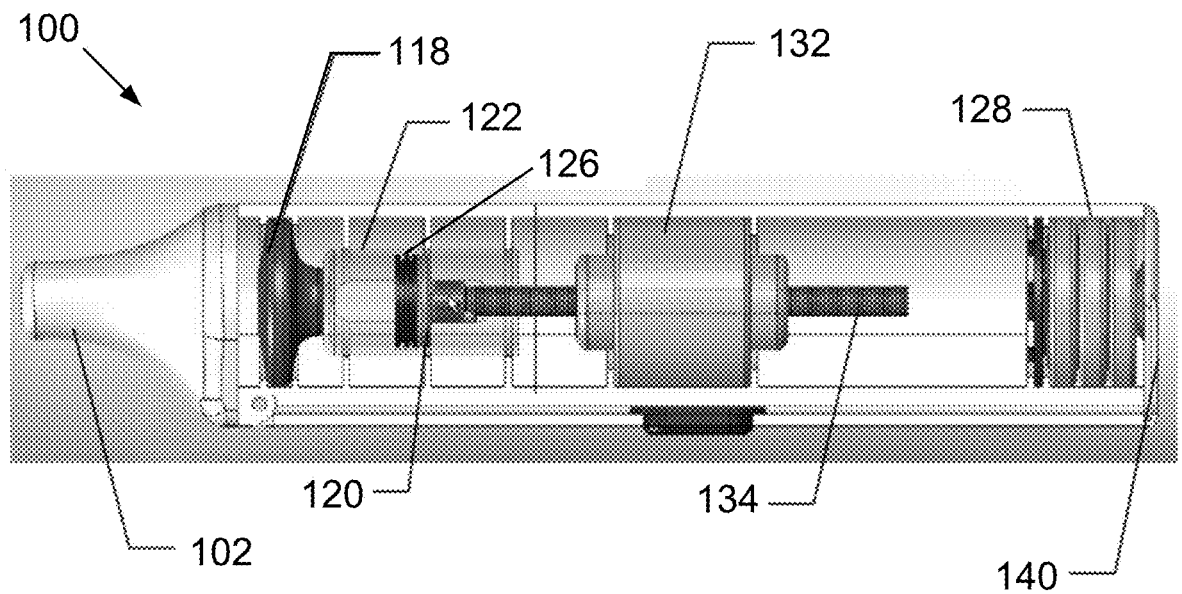

With reference to FIGS. 9 and 10, the tapered end 123 includes an opening 125 through which the liquid passes when the stopper 126 advances toward the tapered end 123. In particular the tapered end 123 is inserted with the opening 127 when the cartridge 122 is inserted into the upper housing component 106, as indicated by the dashed line extending between FIGS. 9 and 10. Thus, when inserted, the tapered end 123 is located within an opening 127 of the mesh assembly 118 (seen in FIG. 4).

Of course, it will be appreciated that in the electronic device 100 the stopper 126 is not attached to the threaded shaft 134 and, therefore, is not directly driven by rotation of the threaded shaft 134 by the motor 132. Instead, the plunger 120 attached to the end of the threaded shaft 134 is directly driven by rotation of the threaded shaft 134 by the motor 132, which causes the plunger 120 to advance into engagement with the stopper 126 and push the stopper toward the taper end 123. This advancement of the plunger 120 and retraction back is illustrated in the sequence seen in FIGS. 11 through 14, which are partial internal views of the electronic device 100.

It will be appreciated from this sequence of FIGS. 11 through 14 that the components are arranged in-line. In particular, the mouthpiece 102, the mesh assembly 118, and the cartridge 122 containing the liquid are arranged sequentially along a longitudinal axis 90 (seen in FIG. 11) of the device 100 in said order, with the mesh assembly 118 being located between the mouthpiece 102 and the liquid to be aerosolized. The stopper 126, plunger 120, and shaft 134 similarly are arranged along the longitudinal axis 90 of the device 100. Additionally, the motor 132 and batteries 128 also are arranged along the longitudinal axis 90 of the device 100.

When the liquid passes through the opening 125 into the opening 127 it contacts a mesh disk 146 (perhaps best seen in FIG. 15) of the mesh assembly. The mesh disk 146 is held or retained in the mesh assembly 118 by an annular plate 144 similar to a washer. The mesh disk 146 preferably is formed from a piezoelectric material (or "piezo") having small openings or holes 148 formed therein for the passage of small droplets of the liquid of a consistent size when the piezo mesh disk is caused to vibrate. This aerosolizes the liquid producing an aerosol. Preferably the droplets produced are between 1- and 4-micron aerosol droplets.

This sequence 400 of steps is illustrated in FIG. 15. Indeed, FIG. 15 includes a picture of an aerosol for inhalation that is actually produced by the vibrating piezo mesh disk. The aerosol produced by the vibrating mesh is a fine particle, low velocity aerosol that is believed to be optimum for central and deep lung deposition.

Figure 13:
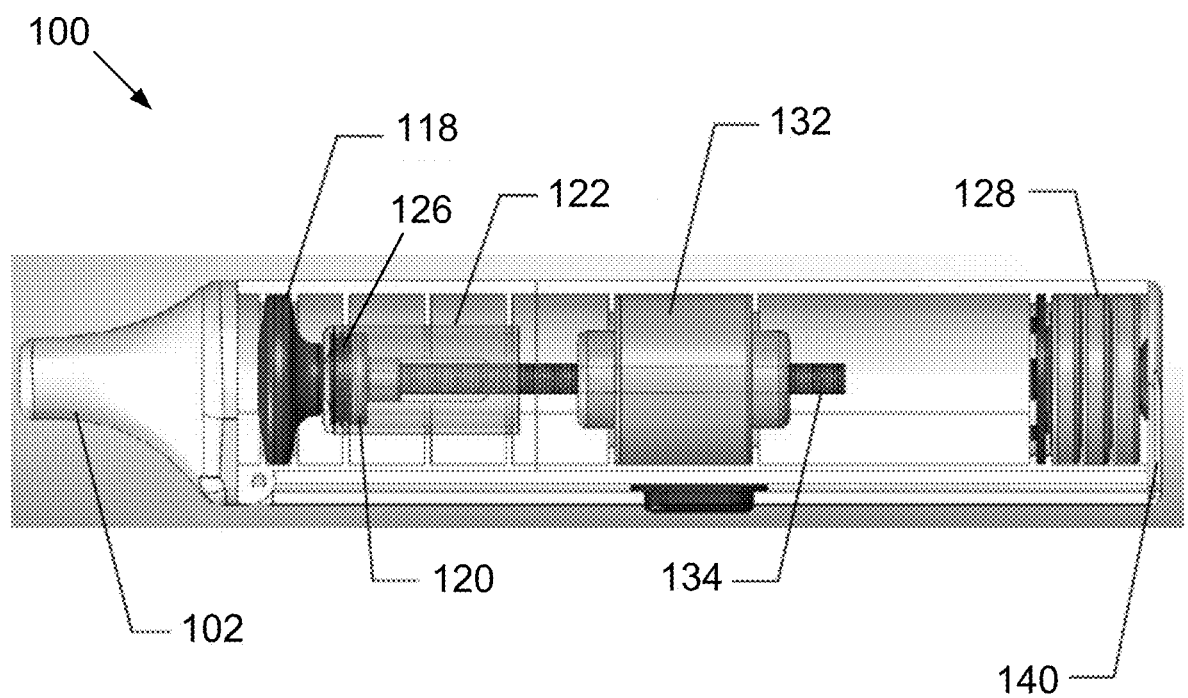
Figure 14:
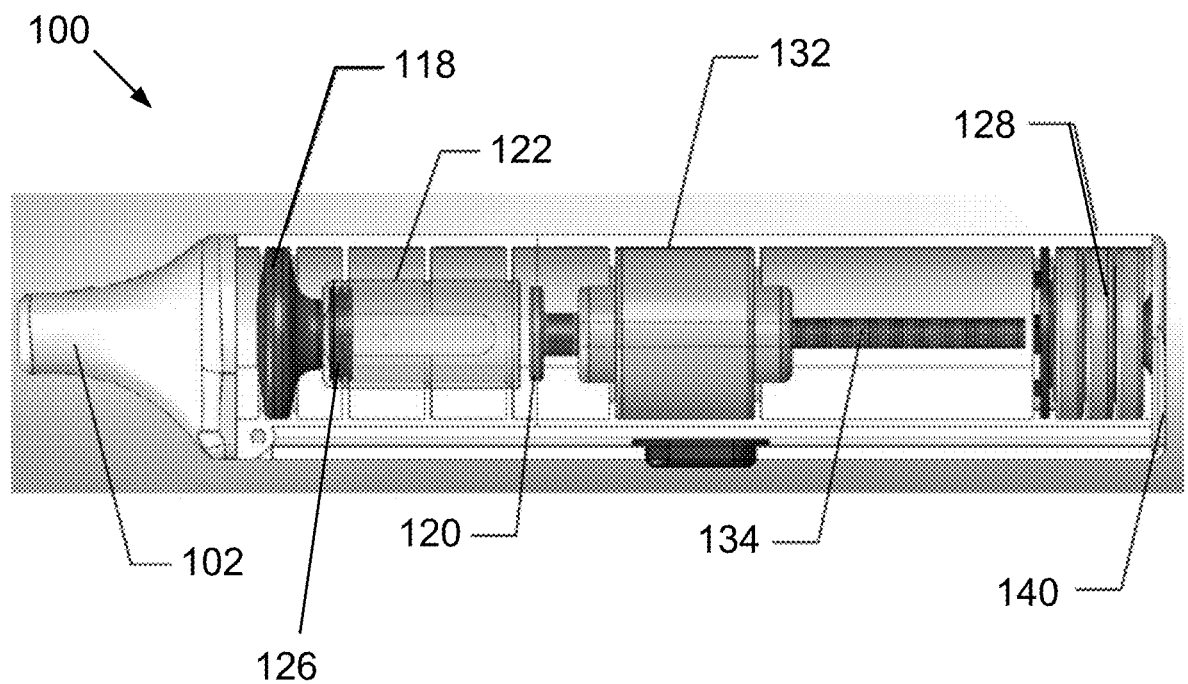

After the plunger 120 has been advanced through the entire cylinder 124 of the cartridge 122 (at which point the cartridge 122 is depleted of the liquid and is empty, as illustrated in FIG. 13), the motor 132 rotates the threaded drive shaft 134 in a reverse direction to return the plunger 120 to the retracted position, as seen in FIG. 14.

Figure 16:
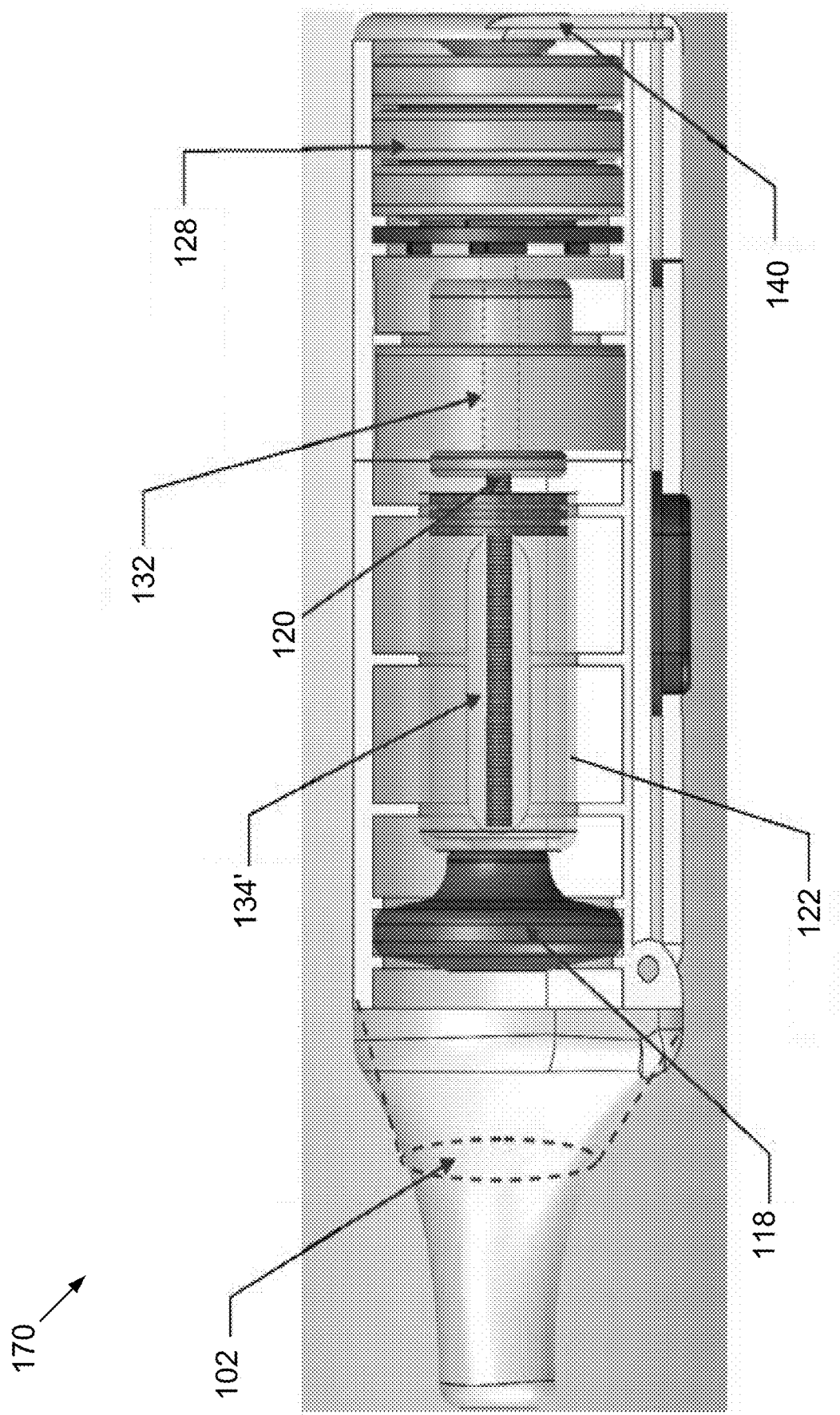
FIG. 16 is a partial internal view of another preferred electronic device in accordance with one or more aspects and features of the invention, wherein component 122 is rendered transparent in the figure for illustration.

An alternative is illustrated in FIG. 16, which is a partial internal view of another electronic device 170 in accordance with one or more aspects and features of the invention. In this device 170, the cartridge includes the threaded shaft 134' extending therethrough. The other components illustrated and having the same reference numbers as those with respect to device 100 are the same.

FIG. 17 is a transparent view of internal components of another preferred electronic device 300 in accordance with one or more aspects and features of the invention. The device 300 comprises a number of components that are arranged in-line along a longitudinal axis 390 of the device 300. These components include a mouthpiece 302 from which aerosol produced by the device 300 can be inhaled; a mesh assembly 304 comprising a vibrating mesh and aperture plate; a liquid container 306 comprising a cartridge or reservoir combined with a threaded shaft 308 that longitudinally extends within the container 306 and a stopper 310 that moves longitudinally within the container 306 along the shaft 308 to ensure the liquid moves towards and stays in contact with the vibrating mesh; and a motor and battery assembly 312 that drives rotation of the shaft 308 and consequent movement of the stopper 310 within the container 306.

Figures 18, 19:
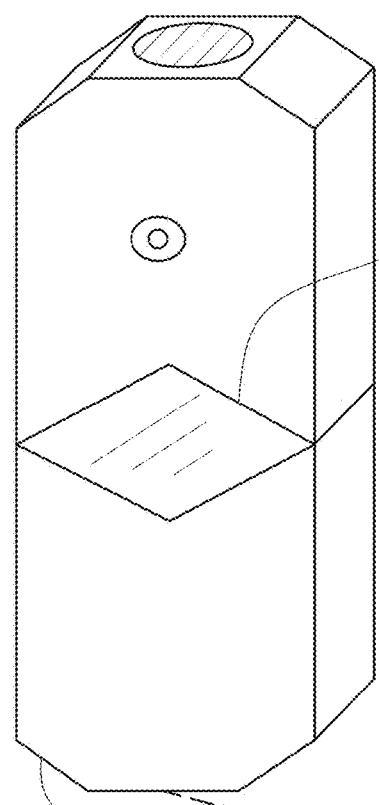
FIG. 18 is a schematic illustration of yet another preferred electronic device in accordance with one or more aspects and features of the invention.
FIG. 19 is a partial schematic illustration of an electromagnetic cartridge of the electronic device of FIG. 18, wherein the outer housing is rendered transparent in the figure for illustration.
Figure 20:
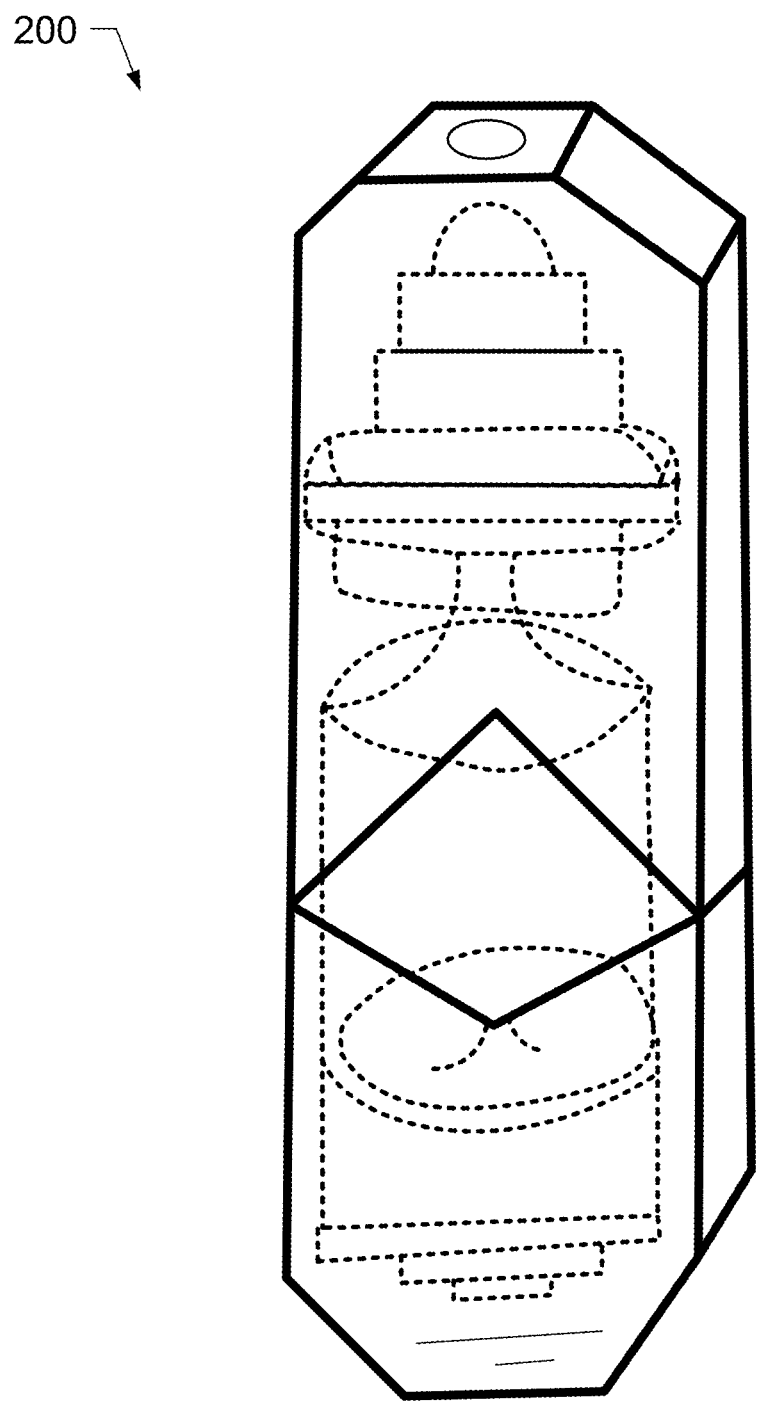
FIG. 20 is an internal schematic illustration of the electronic device of FIG. 18, wherein the outer housing is rendered transparent in the figure for illustration.

Yet another alternative is illustrated schematically in FIGS. 18-20. Specifically, FIG. 18 is a schematic illustration of yet another preferred electronic device 200 in accordance with one or more aspects and features of the invention; FIG. 19 is a partial schematic illustration of an electromagnetic cartridge of the electronic device 200; and FIG. 20 is an internal schematic illustration of the electronic device 200. With reference to FIGS. 18 and 19, electronic device 200 preferably comprises an electromagnetic propulsion system cartridge (e.g., an electromagnetic syringe pump cartridge 201 having cartridge housing 203) that is utilized to push the liquid into contact with the vibrating mesh when the device 200 is activated. The electronic device 200 includes a window 202. Additionally, the electromagnetic cartridge includes a magnetic stopper 204, an anode 206, a cathode, and a magnetic ring 208.

Other contemplated ways of pumping, pushing, or otherwise forcing the liquid into contact with the vibrating mesh include using a solenoid pump, a capillary tube, and a vacuum pump. Gravity may also be used when the electronic device is not intended to be orientation-agnostic in use. In each instance regardless of the manner in which the liquid is pushed from the cartridge into contact with the vibrating mesh, the liquid preferably is supplied to the vibrating mesh at a generally constant pressure whereby a generally uniform aerosol is produced. This is preferably done regardless of the orientation of the electronic device. The electronic device also preferably comprises a reservoir for the liquid. In some embodiments, the reservoir is an anti-pyrolysis vape reservoir with no smoldering and no combustion. In some embodiments, the liquid of the device features a thermostable liquid carrier.

Circuitry (not shown for clarity of illustration) preferably is included in each electronic device for controlling actuation of the vibrating mesh. The circuitry also preferably controls actuation of the pump mechanism for pushing the liquid into contact with the vibrating mesh at a generally constant pressure. A printed circuit board may be included, and an application specific integrated circuit may be included. A microcontroller also may be included (e.g., microchip 8-bit microcontroller-based piezo mesh disk driver board). The microcontroller preferably is located within the lower housing component when included, but in some embodiments the microcontroller may be located within the upper housing component.

Figure 21:
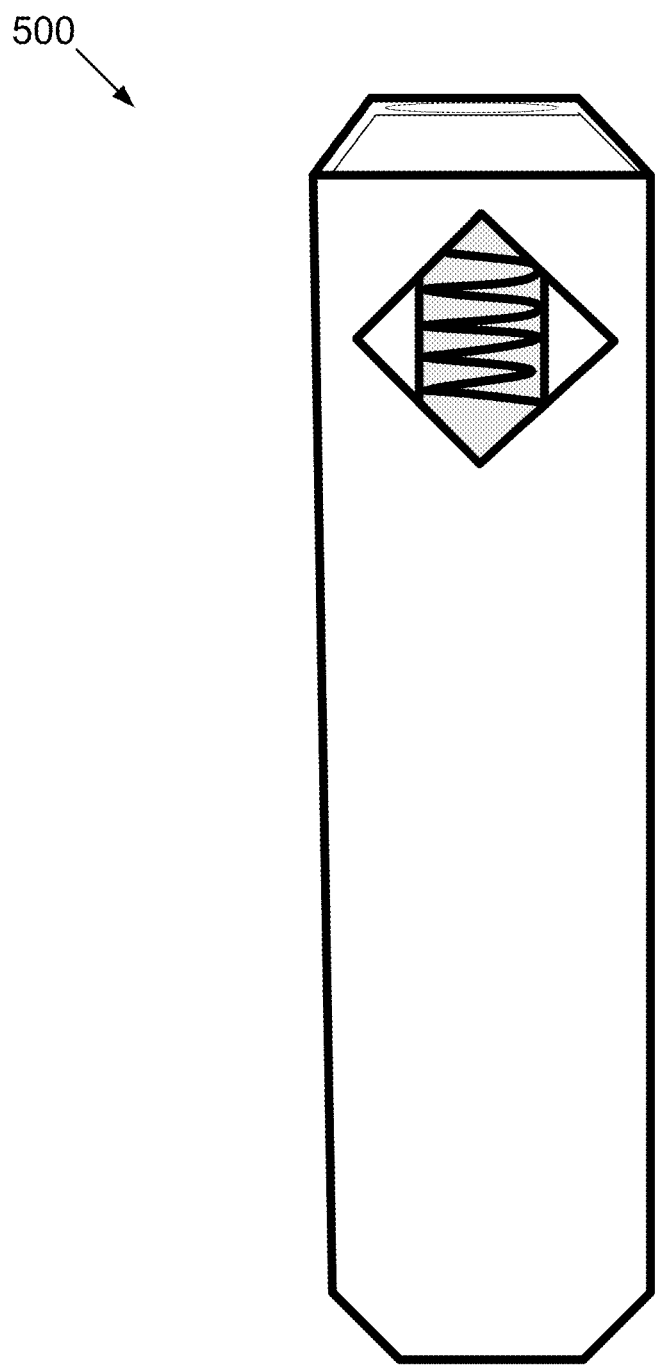
FIG. 21 is a perspective view of yet another preferred electronic device comprising a vibrating mesh in accordance with one or more aspects and features of the invention.

FIG. 21 is a perspective view of yet another preferred electronic device 500 comprising a vibrating mesh in accordance with one or more aspects and features of the invention, and FIG. 22 is an internal schematic illustration thereof. This preferred electronic device 500 comprises a mouthpiece 502 and an aerosol tunnel 504 that extends from the mouthpiece 502 to a double vibrating mesh 506 within the device 500. The vibrating-mesh device 500 also includes a liquid reservoir and cartridge 508 positioned above a stopper 510, which is movable toward the mesh 506 in order to keep a liquid in the reservoir in contact with the mesh 506.

Ultrasonic Nebulizer

In addition to the foregoing electronic devices disclosed herein, and with reference to FIGS. 23-27, alternative electronic devices now are disclosed that preferably are used to aerosolize liquid drugs using a transducer in the form of an ultrasonic vibrating structure that does not comprise a vibrating mesh material, and which are sometimes referred to herein and in the incorporated priority documents as an "ultrasonic nebulizer". The ultrasonic nebulizer may have the liquid drug in direct contact with the transducer, preferably in the form of a piezoelectric transducer; however, the direct contact between the liquid drug and the piezoelectric transducer may cause the temperature of the liquid drug to increase due to heating of the transducer. Accordingly, in some preferred embodiments represented by FIGS. 23-27, the ultrasonic nebulizer comprises an interface between the transducer and the liquid drug. For example, a separate volume of water (or other fluid) may act as an interface between the transducer and the reservoir for the liquid drug, which interface reduces the effects of heating as the liquid drug is not in direct contact with the transducer. Other structures and materials may be used as the interface instead of water, as disclosed below. Moreover, to further reduce the heating effects of the piezo-electric transducer, lower frequencies or lower frequency ranges may be used (e.g., frequencies of approximately 1.2 MHz). In some embodiments, the frequency of the vibrating structure is lower than a frequency utilized in a homogenization process of the liquid to be aerosolized in order to ensure survivability and stability of ananoemulsion. In some embodiments, some residual mass may be trapped in the ultrasonic nebulizer; however, since there is no gas source to transport the aerosol out of the ultrasonic nebulizer during exhalation, little to no leaking occurs.

This alternative electronic device 600 in the form of an ultrasonic nebulizer is now described with reference to the drawings and comprises a removable cartridge 602 as well as a coupling agent interface and heat barrier 604. The cartridge 602 attaches or slides into place on a cartridge mounting 607 of the housing. Additionally, the cartridge may "snap fit" within the housing. In other examples, other attachment means may be used to couple the cartridge 602 to the housing of the device 600. For example, the cartridge may be placed in the housing of the device 600 and secured by a magnet. The cartridge may be a disposable, single-use cartridge; in other embodiments, the cartridge 602 may be a multiple-use cartridge that is removed from, refilled, and then reinstalled in the housing of the device 600.

Because of the coupling agent interface and heat barrier 604, which blocks heating of the liquid drug 606, the ultrasonic device 600 is believed to produces a carcinogen-free aerosol for drug delivery. Specifically, the electronic device 600 preferably utilizes vibrations of a transducer in the form of a piezo-electric material such as a crystal that is located within a transducer sleeve or pocket 608 in the removable cartridge 602. These vibrations are transmitted through the coupling agent interface and heat barrier 604 to the liquid drug, which causes an aerosol to be generated from the liquid drug. The coupling agent interface may comprise a fluid, such as water; a membrane including, for example, a gel membrane; or another material.

Indeed, in some preferred embodiments, the coupling agent comprises a fluid coupler, one example of which is the C4F Coupling fluid sold under the brand SoundSafe®. In some preferred embodiments, the coupling agent is gel based, an example of which is the ultrasound gel sold under the brand CLEAR® by Aquasonic. In some preferred embodiments, the coupling agent is a gel pad, one example of which is the ultrasound gel pad sold under the brand Aquaflex® by Parker Laboratories. A coupling membrane may be similar to the consistency of "standoff pads". Additionally, the membrane may be a gel membrane. Furthermore, the membrane may be hydrophobic. Other coupling agents may be used to block heat from the liquid drug. In these variations, the coupling agent interface transmits ultrasonic vibrations to the liquid, but limits increase in temperature that would otherwise occur in the liquid to be aerosolized.

Moreover, "vapes" on the market typically utilize heat as a way to aerosolize the e-liquid including the desired compounds therein (e.g., nicotine) or supplements such as B12, THC/CBD and other drugs or stimulants. However, toxic byproducts like formaldehyde—a recognized Group 1 Carcinogen for cancer—are created when heat is used to aerosolize, and these toxic byproducts are unfortunately inhaled by the person. For example, when liquids are heated, the liquids undergo a thermochemical reaction producing unwanted emissions; these unwanted emissions of the toxic byproducts are believed to cause harm from inhalation exposure. When used for vaping, the electronic device 600 produces an aerosol that advantageously avoids toxic byproducts created by conventional vapes.

The ultrasonic device 600 is advantageously efficient (with high vibration frequency) for drug administration into the lungs. Additionally, high vibration intensity associated with a low ventilation level is preferable for the delivery of drugs deep into the lungs.

The ultrasonic device 600 may also be designed to provide different flow rates. For example, the device may include an active pump or passive pump. Additionally, the output rate or pressure supplied by the pump may be adjusted to provide different flow rates. In other examples, gravitational, electromagnetic, pneumatic (e.g., pressurized), or capillary forces may be used for delivery of the liquid to be aerosolized.

As illustrated, the removable cartridge 602 preferably houses the coupling agent (fluid or gel, etc.) as well as the liquid drug to be aerosolized. The cartridge 602 preferably comprises a sleeve or pocket 608 for the transducer and a membrane 604 that comprises the coupling agent. For example, the cartridge 602 may comprise a thin gel membrane with a coupling agent, which advantageously enables the ultrasonic device to deliver an emissions/carbonyl free/volatile constituent free experience to a person. The coupling agent also advantageously allows for the effective delivery of potentially thermosensitive substances.

When the vibration intensity is sufficient, cavitation occurs, and large and small droplets are generated. Large droplets may fall or drop into the liquid reservoir or may be thrown onto the side of the nebulizer and recycled. Additionally, small droplets may be stored in the nebulization chamber to be inhaled by a person. Ventilation enables airflow to cross the nebulizer and to expel the aerosol droplets.

For a given ultrasonic nebulizer, the vibration frequency of the piezoelectric crystal may be fixed, often in the range of 1-2.5 MHz. In some preferred embodiments, the vibration intensity is adjustable by modifying vibration amplitude. Additionally, the ventilation level preferably is adjustable. The coupling agent blocks heat from the liquid to be aerosolized, which is particularly advantageous when using thermosensitive drugs and in reducing or preventing unwanted emissions byproducts.

Figure 26:
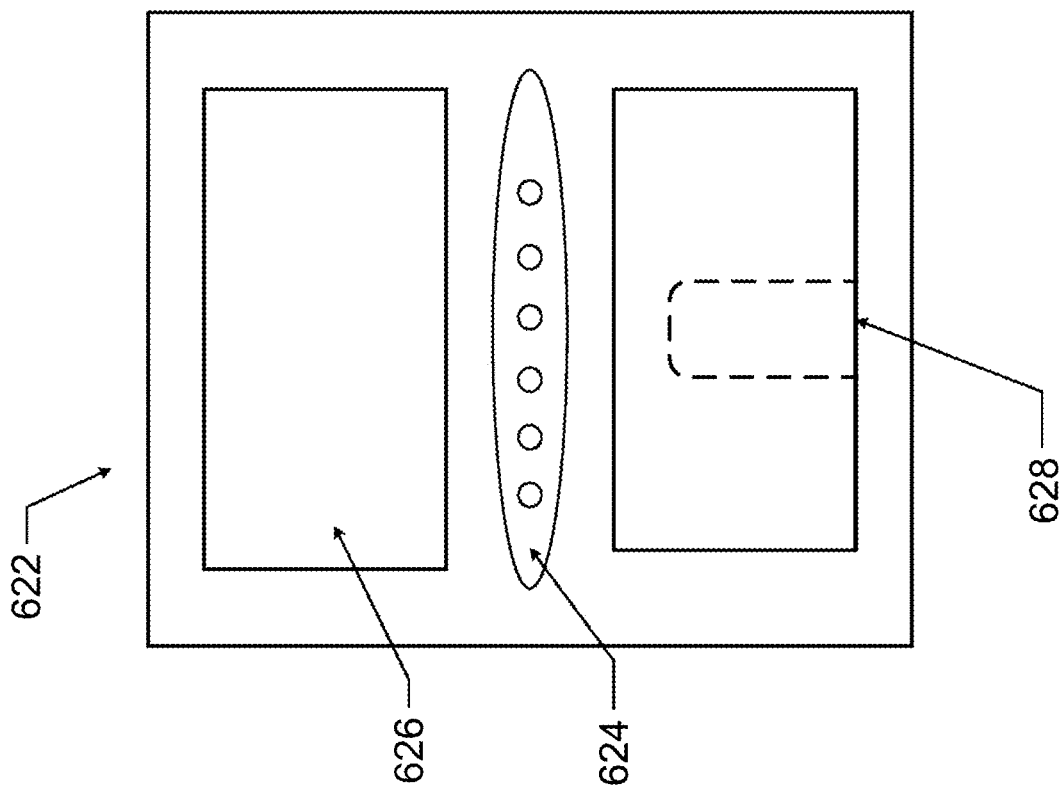
FIG. 26 is a schematic plan view of a side of another cartridge for a preferred electronic device comprising an ultrasonic device in accordance with one or more aspects and features of the invention.
Figure 25:
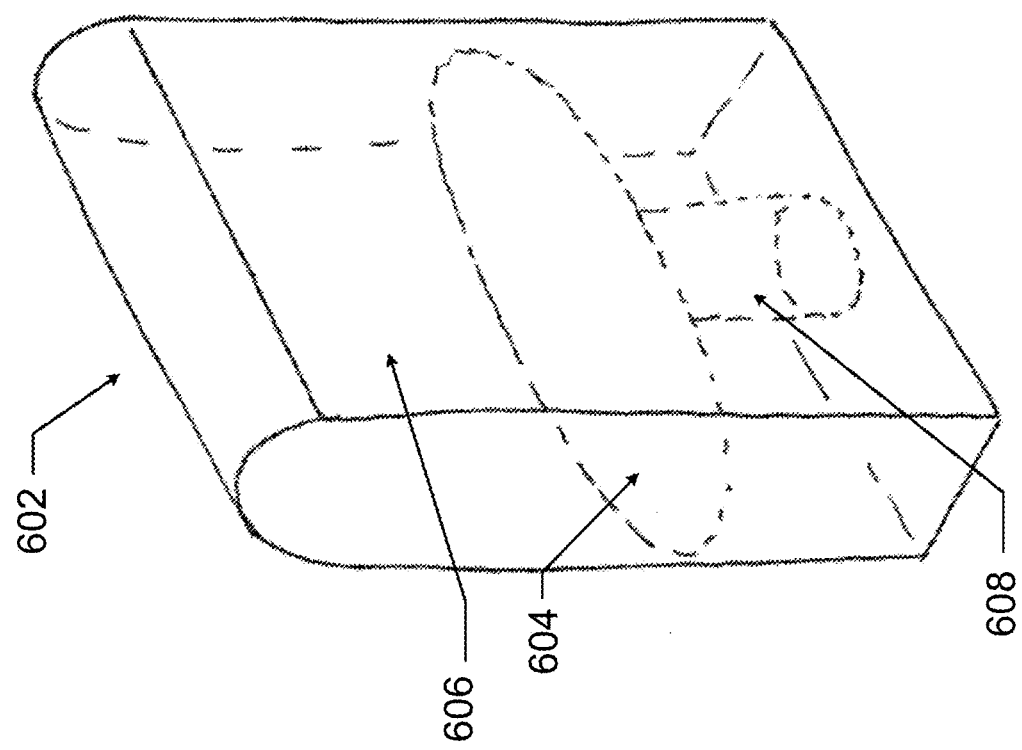
FIG. 25 is a schematic perspective view of a cartridge representative of the device system represented in FIG. 23 in accordance with one or more aspects and features of the invention.

An alternative removable cartridge 622 is shown in FIG. 26, wherein the reservoir for the liquid drug 626 is housed above the membrane 624 whereby the liquid drug may seep into and saturate the membrane. The transducer then creates an aerosol from the liquid drug thereby contained within the membrane.

For clarity of illustration, it will be appreciated that the inlets, outlets, and ventilation features are not shown in the electronic devices and cartridges of FIGS. 23-26.

The above-described electronic devices described herein are person-activated or breath activated. In particular in some embodiments, the above-described electronic devices each detects inhalation by a person and activates in response; and in some embodiments, the above-described electronic devices each includes a graphical person interface with selectable icons and menus to program and adjust operational parameters of the electronic device, including activation for producing the aerosol for inhalation.

Based on the foregoing description, it will be readily understood by those persons skilled in the art that the invention has broad utility and application. Electronic devices of the invention can be utilized to deliver liquids comprising supplements, drugs, or therapeutically effective amounts of pharmaceuticals using an aerosol having particles of a size that can easily be inhaled. The aerosol can be used, for example, by a patient within the bounds of an inhalation therapy, whereby the liquid containing a supplement, therapeutically effective pharmaceutical, or drug reaches the patient's respiratory tract upon inhalation. Desired compounds such as nicotine, flavoring, and supplements like B12, can be received by a person through inhalation without the toxic byproducts like formaldehyde—a recognized Group 1 Carcinogen for caner—that is currently being created during heating in conventional vapes. Electronic devices of the invention further can be used in the marijuana industries, but only where legal, for delivery of cannabinoids and CBD oils and the like. Moreover, many embodiments and adaptations of the invention other than those specifically described herein, as well as many variations, modifications, and equivalent arrangements, will be apparent from or reasonably suggested by the invention and the foregoing descriptions thereof, without departing from the substance or scope of the invention.

Accordingly, while the invention has been described herein in detail in relation to one or more preferred embodiments, it is to be understood that this disclosure is only illustrative and exemplary of the invention and is made merely for the purpose of providing a full and enabling disclosure of the invention. The foregoing disclosure is not intended to be construed to limit the invention or otherwise exclude any such other embodiments, adaptations, variations, modifications or equivalent arrangements, the invention being limited only by the claims appended hereto and the equivalents thereof

What is claimed is:

1. An apparatus for producing an aerosol for inhalation by a person, the apparatus comprising:
   (a) a liquid container containing a liquid mixture which when aerosolized is intended for inhalation by a person;
   (b) a transducer comprising a mesh material that, when actuated, vibrates resulting in aerosolizing of the liquid mixture from the container such that the aerosol may be inhaled by a person; and
   (c) means for pressing the liquid mixture into contact with the mesh material regardless of the orientation of the liquid container;
   (d) wherein the liquid mixture to be aerosolized comprises an inhalable liposomal carrier including encapsulated tetrahydrocannabinol or encapsulated cannabidiol deliverable to the respiratory tract.

2. The apparatus of claim 1, wherein the liposomal carrier comprises a liposomal nanoemulsion.

3. The apparatus of claim 1, wherein the liquid mixture comprises nanoparticles.

4. The apparatus of claim 1, wherein the liquid mixture comprises nicotine.

5. The apparatus of claim 1, wherein the liquid mixture comprises an aqueous liquid.

6. The apparatus of claim 1, wherein the transducer and the mesh material form a piezo mesh disk.

7. The apparatus of claim 1, wherein the means comprises a motor, a threaded shaft that is rotated by the motor, and a stopper on the threaded shaft that is advanced along the shaft by rotation of the threaded shaft for pushing the liquid mixture toward the mesh material.

8. An apparatus for use with an electronic device for producing an aerosol for inhalation by a person, the apparatus comprising:
   (a) a liquid container containing a liquid which when aerosolized is intended for inhalation by a person; and
   (b) a transducer that, when actuated, causes the liquid from the container to be aerosolized such that the aerosol may be inhaled by a person;
   (c) wherein the liquid comprises an active agent entrapped by liposomes;
   (d) wherein the transducer comprises a mesh material that vibrates when the transducer is actuated, thereby resulting in aerosolization of the liquid; and
   (e) wherein the transducer and the mesh material form a piezo mesh disk; and
   (f) further comprising means for pressing the liquid into contact with the mesh material regardless of the orientation of the liquid container.

9. The apparatus of claim 8, wherein the active agent comprises nicotine.

10. The apparatus of claim 8, wherein the active agent comprises tetrahydrocannabinol.

11. The apparatus of claim 8, wherein the active agent comprises cannabidiol.

12. The apparatus of claim 8, wherein the liquid comprises nanoparticles formed by an oil droplet covered by a monolayer of phosphatidylcholine.

13. The apparatus of claim 8, wherein the means comprises a motor, a threaded shaft that is rotated by the motor, and a stopper on the threaded shaft that is advanced along the shaft by rotation of the threaded shaft for pushing the liquid mixture toward the mesh material.

14. An apparatus for producing an aerosol for inhalation by a person, the apparatus comprising:
   (a) a liquid container containing a liquid mixture comprising a nanodispersion which when aerosolized is intended for inhalation by a person;
   (b) a transducer comprising a mesh material that, when actuated, vibrates resulting in aerosolizing of the liquid mixture from the container such that the aerosol may be inhaled by a person; and
   (c) means for pressing the liquid mixture into contact with the mesh material regardless of the orientation of the liquid container.

15. The apparatus of claim 14, wherein the liquid mixture comprises nicotine.

16. The apparatus of claim 14, wherein the liquid mixture comprises tetrahydrocannabinol.

17. The apparatus of claim 14, wherein the liquid mixture comprises cannabidiol.

18. The apparatus of claim 14, wherein the liquid mixture comprises nanoparticles formed by an oil droplet covered by a monolayer of phosphatidylcholine.

19. The apparatus of claim 14, wherein the transducer and the mesh material form a piezo mesh disk.

20. The apparatus of claim 14, wherein the means comprises a motor, a threaded shaft that is rotated by the motor, and a stopper on the threaded shaft that is advanced along the shaft by rotation of the threaded shaft for pushing the liquid mixture toward the mesh material.

* * * * *